(12) United States Patent
Srinivasan et al.

(10) Patent No.: US 11,548,866 B1
(45) Date of Patent: Jan. 10, 2023

(54) THERAPEUTIC COMPOUNDS AND METHODS OF USE THEREOF

(71) Applicant: LIGATURE THERAPEUTICS PTE. LTD., Singapore (SG)

(72) Inventors: Rajavel Srinivasan, Singapore (SG); Wei Hung, Singapore (SG)

(73) Assignee: LIGATURE THERAPEUTICS PTE. LTD., Singapore (SG)

( * ) Notice: Subject to any disclaimer, the term of this patent is extended or adjusted under 35 U.S.C. 154(b) by 0 days.

(21) Appl. No.: 17/532,698

(22) Filed: Nov. 22, 2021

(51) Int. Cl.
| | |
|---|---|
| *C07D 401/04* | (2006.01) |
| *C07D 401/14* | (2006.01) |
| *A61P 35/00* | (2006.01) |
| *C07D 241/04* | (2006.01) |

(52) U.S. Cl.
CPC ............ *C07D 401/04* (2013.01); *A61P 35/00* (2018.01); *C07D 241/04* (2013.01); *C07D 401/14* (2013.01)

(58) Field of Classification Search
CPC ...... C07D 401/04; C07D 401/14; A61P 35/00
See application file for complete search history.

(56) References Cited

U.S. PATENT DOCUMENTS

| | | | |
|---|---|---|---|
| 7,759,383 B2 | 7/2010 | Wang | |
| 8,236,805 B2 * | 8/2012 | Gilbert | ................ C07D 409/12 544/359 |
| 2005/0288287 A1 | 12/2005 | Fotouhi | |
| 2009/0312310 A1 | 12/2009 | Kawato | |
| 2010/0048593 A1 | 2/2010 | Weissman | |

* cited by examiner

*Primary Examiner* — Samira J Jean-Louis

(57) ABSTRACT

There are provided new inhibitors of MDM2. Also provided are methods of synthesizing the agents, pharmaceutical formulations including the agents, and methods of using the agents to treat, ameliorate or cure diseases characterized by MDM2 over-expression or malfunction.

15 Claims, No Drawings

THERAPEUTIC COMPOUNDS AND METHODS OF USE THEREOF

TECHNICAL FIELD

The present invention relates, in general terms, to therapeutic compounds for use as modulators of ubiquitination. The present invention also relates to methods of use thereof.

BACKGROUND

Drug development is a lengthy, complex, and costly process, entrenched with a high degree of uncertainty that a drug will actually succeed. This is further acerbated by the unknown pathophysiology for many disorders which makes target identification and drug development challenging. Further, animal models often cannot recapitulate an entire disorder or disease, and hence critical decisions about a pipeline drug are often made at too late a stage at too high a cost. Challenges are also present from the heterogeneity of the patient population. All in all, the inability to target and modulate certain classes of bio macromolecules limits our ability to develop effective anti-cancer drugs.

The p53 tumor suppressor is a principal mediator of growth arrest, senescence, and apoptosis in response to a broad array of cellular damage. Rapid induction of high p53 protein levels by various stress types prevents inappropriate propagation of cells carrying potentially mutagenic, damaged DNA. p53 can kill cells via a dual transcription-dependent and -independent function in the nucleus and at the mitochondria. It has been demonstrated that cellular p53 protein levels are the single most important determinant of its function. In normal unstressed cells, p53 is a very unstable protein with a half-life ranging from 5 to 30 min, which is present at very low cellular levels owing to continuous degradation largely mediated by MDM2 (Murine Double Minute 2). Conversely, a hallmark of many cellular stress pathways such as DNA damage, hypoxia, telomere shortening, and oncogene activation is the rapid stabilization of p53 via a block of its degradation. MDM2 has emerged as the principal cellular antagonist of p53 by limiting the p53 tumor suppressor function. Moll and Petrenko, Molecular Cancer Research 1:1001-1008 (2003).

MDM2 inhibitors interfere with the binding of MDM2 oncoprotein to the tumor suppressor p53 protein, and serve as a pharmacological p53 activator. Emerging evidence suggests that p53 dysfunction also fuels inflammation and supports tumor immune evasion and, thus, p53 dysfunction serves as an immunological driver of tumorigenesis (Guo G, Cancer Research, 2017; 77(9):2292).

MDM2 and p53 are part of an auto-regulatory feed-back loop (Wu et al., Genes Dev. 7:1126 (1993)). MDM2 is transcriptionally activated by p53, and MDM2, in turn, inhibits p53 activity by at least three mechanisms (Wu et al., Genes Dev. 7:1126 (1993)). First, MDM2 protein directly binds to the p53 transactivation domain, and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

MDM2 is transcriptionally activated by p53 and MDM2, in turn, inhibits p53 activity by at least three mechanisms. Wu et al., Genes Dev.7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 promotes p53 degradation.

Small-molecule inhibitors that target the p53-MDM2 interaction have therapeutic potential for treating cancer and other diseases. Chene, Nat.Rev. Cancer 3:102 (2003) and Vassilev et al., Science 303:844 (2004). Antagonists of the p53-MDM2 interaction are described in U.S. Pat. Nos. 7,759,383; 7,737,174; 8,518,984; 8,680,132; 8,629,141; 6,617,346; 6,734,302; 7,132,421; 7,425,638; 7,579,368; 7,060,713; 7,553,833; 6,916,833; 7,495,007; 7,638,548; 7,576,082; 7,625,895; and 7,083,983; and U.S. Patent Application Publication Nos. 2005/0288287; 2009/0143364; 2009/0312310; 2006/0211718; 2010/0048593; 2005/0227932; 2008/0261917; 2009/0227542; 2008/0171723; 2006/0211757; 2005/0137137; 2002/0132977; and 2009/0030181.

There is an ongoing need for new agents, e.g., small molecules, for treating cancer and other diseases responsive to the disruption or prevention of the MDM2-p53 interaction.

SUMMARY

In various embodiments, the present invention provides a novel class of chemotherapeutic agents based upon the principal of inhibition of MDM2, formulations including these agents and methods of using the agents in the treatment of disease, e.g., proliferative disease.

In various embodiments, the present invention provides MDM2 inhibitors represented by Formula I, below, and a pharmaceutically acceptable salt or solvate thereof, collectively referred to as "compounds of the invention". The MDM2 inhibitors are, in various embodiments, useful in treating diseases or conditions wherein inhibition of MDM2 provides a benefit.

In some embodiments, the present invention provides methods of treating a condition or disease by administering a therapeutically effective amount of a compound of the invention to a subject, e.g., a human, in need thereof. The disease or condition is treatable by inhibition of MDM2. Exemplary diseases are cancer, chronic autoimmune disorder, inflammatory condition, proliferative disorder, sepsis, or a viral infection.

Also provided are methods of preventing the proliferation of unwanted proliferating cells, such as in cancer, in a subject. The method includes administering a therapeutically effective amount of a MDM2 inhibitor of the invention to a subject at risk of developing a condition characterized by unwanted proliferating cells. In some embodiments, the compound of the invention reduces the proliferation of unwanted cells by inducing apoptosis in those cells.

In various embodiments, the present invention provides a method of inhibiting MDM2 proteins in a subject. The method comprises administering to the subject an effective amount of at least one compound of the invention. In this context, an effective amount is the amount required to inhibit MDM2 in the subject to whom the compound of the invention is administered.

In some embodiments, the present invention provides a method of reducing the amount of MDM2 protein (or activity) within a cell of a subject, e.g., a human patient in need thereof. The method includes administering an effective amount of a compound of the invention to the subject. In this context, an effective amount is an amount of a compound of the invention required to reduce the amount of MDM2 protein (or activity) within a cell of the subject.

In an exemplary embodiment, the invention provides a pharmaceutical composition comprising a compound of the invention and an excipient and/or pharmaceutically acceptable carrier.

In some embodiments, the present invention provides a composition comprising a compound of the invention and an excipient and/or pharmaceutically acceptable carrier for use treating diseases or conditions wherein inhibition of MDM2 proteins provides a benefit, e.g., cancer.

In various embodiments, the invention provides a composition comprising: (a) a compound of the invention; (b) a second therapeutically active agent; and (c) optionally an excipient and/orpharmaceutically acceptable carrier.

In some embodiments, the invention provides a compound of the invention for use in treatment of a disease or condition of interest, e.g., cancer.

In various embodiments, the invention provides a use of a compound of the invention for the manufacture of a medicament for treating a disease or condition of interest, e.g., cancer.

In some embodiments, the invention provides a kit comprising a compound of the invention, and, optionally, a packaged composition comprising a second therapeutic agent useful in the treatment of a disease or condition of interest, and a package insert containing directions for use in the treatment of a disease or condition, e.g., cancer.

In various embodiments, the invention provides a method of treating a subject having a cancer, the method comprising:
(a) determining a level of expression of MDM2 in a biological sample taken from the subject; and
(b) administering a therapeutically effective amount of a compound of the invention to the subject following determining the level of expression of MDM2 present in the biological sample.

In an exemplary embodiment, the MDM2 expression is abnormal. In various embodiments, the MDM2 is overexpressed.

Additional embodiments and advantages of the disclosure will be set forth, in part, in the description that follows, and will flow from the description, or can be learned by practice of the invention. The embodiments and advantages of the invention will be realized and attained by means of the elements and combinations particularly pointed out in the appended claims.

It is to be understood that both the foregoing summary and the following detailed description are exemplary and explanatory only, and are not restrictive of the invention as claimed.

In another aspect, the present invention relates to a compound of Formula (I), (II) or (III) or a pharmaceutically acceptable salt, solvate, stereoisomer or prodrug thereof.

In another aspect, the present invention relates to a pharmaceutical composition comprising an effective amount of compound of a Formula set forth herein or a pharmaceutically acceptable salt, solvate, stereoisomer or prodrug thereof, optionally in combination with a pharmaceutically acceptable carrier, excipient or diluent.

In another aspect, the present invention relates to a method of inhibiting MDM2 in a cell, including a step of contacting a compound of a Formula set forth herein with the cell to inhibit MDM2 in the cell.

In another aspect, the present invention relates to a method of treating a disease or condition associated with MDM2 by inhibiting MDM2, thereby treating the disease or condition. The method comprises administering a compound of Formula set forth herein or a pharmaceutically acceptable salt, solvate, stereoisomer or prodrug thereof in a patient in need thereof. In an exemplary embodiment, the compound is administered as a pharmaceutically acceptable formulation.

In another aspect, the present invention relates to a compound of Formula set forth herein or a pharmaceutically acceptable salt, solvate, stereoisomer or prodrug thereof for use as a medicament.

In another aspect, the present invention relates to a compound of Formula set forth herein or a pharmaceutically acceptable salt, solvate, stereoisomer or prodrug thereof for use in the treatment of a disease or condition associated with MDM2, e.g., overexpressed MDM2.

In another aspect, the present invention relates to a use of a compound of Formula set forth herein or a pharmaceutically acceptable salt, solvate, stereoisomer or prodrug thereof in the manufacture of a medicament for the treatment of a disease or condition associated with an overexpressed protein.

In some embodiments, the overexpressed protein is MDM2.

In various embodiments, the disease or condition is selected from hyperplasia and cancer.

DETAILED DESCRIPTION

I. Introduction

The present invention provides a novel class of inhibitors of MDM2. It is an object of the present invention to provide a medicament to improve treatment of a proliferative disease, e.g., cancer, in particular to improve treatment of cancer through inhibition of cell growth (proliferation) and/ or induction of apoptosis.

II. Definitions

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the content clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the terms "compounds herein described", "compounds of the invention" and equivalent expressions refer to compounds described in the present application, e.g., those encompassed by the structural Formulae, optionally with reference to any of the applicable embodiments, and also includes exemplary compounds, as well as their pharmaceutically acceptable salts, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C- enriched carbon are within the scope of the present description. Such compounds are useful, for example, as analytical tools, as probes in biological assays, or as therapeutic agents in accordance with the present description.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen, et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions, p. 268 (E. L. Eliel, Ed., Univ. of Notre Dame Press, Notre Dame, Ind. 1972). In certain embodiments, the invention provides compounds according to a Formula set forth herein which are "optically enriched".

Definitions of specific functional groups and chemical terms are described in more detail below. For purposes of the present description, the chemical elements are identified in accordance with the Periodic Table of the Elements, CAS version, Handbook of Chemistry and Physics, 75$^{th}$, Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th, Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For greater certainty, examples of abbreviations used in the present application are listed in a table in the Examples section.

The number of carbon atoms in a hydrocarbyl or other substituent can be indicated by the prefix "$C_x$-$C_y$," where x is the minimum and y is the maximum number of carbon atoms in the substituent. When reference is made to "x to y membered" heterocyclic ring (e.g., heterocycloalkyl or heteroaryl), then x and y define respectively, the minimum and maximum number of atoms in the cycle, including carbons as well as heteroatom(s). The numbers between the minimum and maximum are fully described by stating these two endpoints, thus $C_1$-$C_6$ discloses $C_1$, $C_2$, $C_3$, $C_4$, $C_5$ and $C_6$.

The prefix "halo" indicates that the substituent to which the prefix is attached is substituted with one or more independently selected halogen atoms. More specifically, the terms "halo" and "halogen" as used herein refer to an atom selected from fluorine (fluoro, —F), chlorine (chloro, —Cl), bromine (bromo, —Br), and iodine (iodo, —I). For example, "haloalkyl" means an alkyl substituent wherein at least one hydrogen atom is replaced with a halogen atom and "haloalkoxy" means an alkoxy substituent wherein at least one hydrogen atom is replaced with a halogen atom.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+(as in N-substituted pyrrolidinyl).

As used herein a "direct bond" or "covalent bond" refers to a single, double or triple bond. In certain embodiments, a "direct bond" or "covalent bond" refers to a single bond. This term is also synonymous with a "zero-order linker".

Where substituent groups are specified by their conventional chemical formulae, written from left to right, they optionally equally encompass the chemically identical substituents, which would result from writing the structure from right to left, e.g., —CH$_2$O— is intended to also recite— OCH$_2$—.

The term "alkyl", by itself or as part of another substituent, means a straight, cyclic or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl. In exemplary embodiments, "Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkenylene" refers to divalent alkenyl groups preferably having from 2 to 8 carbon atoms and more preferably 2 to 6 carbon atoms. Examples include ethenylene (—CH=CH—), and the propenylene isomers (e.g., —CH$_2$CH=CH— and —C(CH$_3$)=CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl CH), propargyl (—CH$_2$C≡CH), pent-2-ynyl (—CH$_2$C≡CCH$_2$—CH$_3$), and the like.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyloxy" refers to the group alkenyl-O— wherein the alkenyl group is as described above.

"Alkynyloxy" refers to the group alkynyl-O— wherein the alkynyl groups is as described above.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

"Haloalkyl" refers to an alkyl group wherein the alkyl group is substituted by one or more halo group as described above. The terms "haloalkenyl", "haloalkynyl" and "haloalkoxy" are likewise defined.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. No more than two heteroatoms may be consecutive, as in, for example, —CH$_2$—NH—OCH$_3$ and —CH$_2$—O—Si(CH$_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

"Aryl" refers to an unsaturated aromatic carbocyclic group having a single ring (eg. phenyl) or multiple condensed rings (e.g., naphthyl or anthryl), preferably having from 6 to 14 carbon atoms. Examples of aryl groups include phenyl, naphthyl and the like.

"Heteroaryl" refers to a monovalent aromatic heterocyclic group which fulfils the Hückel criteria for aromaticity (ie. contains 4n+2 π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl).

Examples of heteroaryl groups include, but are not limited to, azaoxindole, oxazole, pyrrole, imidazole, pyrazole, pyridine, pyrazine, pyrimidine, pyridazine, indolizine, isoindole, indole, indazole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, thiazole, thiadiazoles, oxadiazole, oxatriazole, tetrazole, thiophene, benzo[b]thiophene, triazole, imidazopyridine and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

The term "acyl" refers to a species that include the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. Exemplary acyl groups include H—C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein. In some embodiments, R is selected from H and ($C_1$-$C_6$)alkyl.

'Oxy' or 'oxo' refers to —O—.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Acylene" refers to the group —C(O)—.

"Amino" refers to the group —NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminylacylene" refers to a divalent group group —C(O)NR"— where each R" is independently hydrogen, alkyl, cycloalkyl, aryl, heteroaryl, and heterocyclyl and where each of alkyl, cycloalkyl, aryl, heteroaryl and heterocyclyl is as described herein. As used herein, the divalent group is attached as L—C(O)NR"-(1,4-diazinane or piperazine moiety).

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acylaminylene" refers to the divalent group —NR"C(O)— where each R" is independently hydrogen, alkyl, cycloalkyl, aryl, heteroaryl and heterocyclyl and where each of alkyl, cycloalkyl, aryl, heteroaryl, and heterocyclyl are as described herein. As used herein, the divalent group is attached as L— NR"C(O)-(1,4-diazinane or piperazine) moiety.

"Acyloxy" refers to the groups —OC(O)-alkyl, —OC(O)-aryl, —C(O)O— heteroaryl, and —C(O)O-heterocyclyl where alkyl, aryl, heteroaryl and heterocyclyl are as described herein.

"Aminoacyloxy" refers to the groups —OC(O)NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O— heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like. As used herein, 'cycloalkyl' comprises bridged cycloalkyl, spiro cycloalkyl and fused cycloalkyl. The skilled person would understand that bridged cycloalkyl comprises two or more rings bonded to each other at bridgehead atoms (ring junctions). In fused bicyclic compounds, two rings share two adjacent atoms; i.e. the rings share one covalent bond or the so-called bridgehead atoms are directly connected. In spiro cycloalkyl, two or more rings are linked together by one common atom.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, $R_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond. Spiro heterocyclyl are also included within this definition.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkyl-O—C(S)—, aryl-O—C(S)—, heteroaryl-O—C(S)—, and heterocyclyl-O—C(S)—, where alkyl, cycloalkyl, aryl, heteroaryl and heterocyclyl are as described herein.

"Oxythioacyloxy" refers to groups HO—C(S)—O—, alkyl-O—C(S)—O—, cycloalkyl-O—C(S)—O—, arylO—C(S)—O—, heteroaryl-O—C(S)—O—, and heterocyclyl-O—C(S)—O—, where alkyl, cycloalkyl, aryl, heteroaryl and heterocyclyl are as described herein.

"Phosphorylamino" refers to the groups —NR"—P(O)(R''')(OR"") where R" represents H, alkyl, cycloalkyl, alkenyl, or aryl, R''' represents OR"" or is hydroxy or amino and R"" is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkyl-O—S(O)—NR"—, cycloalkyl-O—S(O)—NR"—, aryl-O—S(O)—NR"—, heteroaryl-O—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkyl-O—S(O)$_2$—NR"—, cycloalkyl-O—S(O)$_2$—NR"—, arylO—S(O)$_2$—NR"—, heteroaryl-O—S(O)$_2$—NR"—, and heterocyclyl-O—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In some embodiments, any of alkyl, heteroalkyl, cycloalkyl, heterocycloalkyl, aryl and heteroaryl is optionally substituted. That is, in some embodiments, any of these groups is substituted or unsubstituted or fused (so as to form a condensed polycyclic group) with one or more groups.

Compounds of the invention may include one or more of these moieties in addition to or instead of the substituent groups explicitly exemplified in this invention. Any of these moieties may be an "aryl group substituent" and/or an "alkyl group substituent".

In some embodiments, substituents for selected radicals are selected from those provided below.

Exemplary substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. In one embodiment, R', R", R'" and R"" are each independently selected from hydrogen, alkyl (e.g., $C_1$, $C_2$, $C_3$, $C_4$, $C_5$ and $C_6$ alkyl). In one embodiment, R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R'" and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R'" and R"" are independently selected from hydrogen and alkyl (e.g., $C_1$, $C_2$, $C_3$, $C_4$, $C_5$ and $C_6$ alkyl). In some embodiments, R', R", R'" and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R'" and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

In various embodiments, one or more substituents are selected from hydroxyl, acyl, acyliminoxy, acylimino, alkyl, alkoxy, alkenyl, aryl, aryloxy, alkynyl, alkenyloxy, alkynyloxy, halo, haloalkyl, aryl, arylene, aryloxy, arylalkyl, arylalkoxy, cycloalkyl, cycloalkenyl, oxy, oxyacyl, acylene, amino, aminylacylene, acylamino, acylaminylene, acyloxy, aminoacyloxy, carboxyl, acylamino, cyano, halogen, nitro, oxyacylamino, oxyacyloxy, oxyacylimino, phosphono, sulfo, phosphorylamino, phosphinyl, heteroaryl, heteroarylalkyl, heteroaryloxy, heterocyclyl, heterocyclylalkyl, heterocyclyloxy, heteroarylene, heterocyclylene, thio, thioacyl, oxythioacyl, oxythioacyloxy, thioacyloxy, sulfinyl, sulfonyl, sulfinylamino, sulfonylamino, oxysulfinylamino, oxysulfonylamino, aminothioacyl, thioacylamino, aminosulfinyl, aminosulfonyl, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

Any of the substituents set forth hereinabove can be a component of a compound of the invention, whether located on one or more of a substituted alkyl, substituted heteroalkyl, substituted aryl or substituted heteroaryl moiety of a compound of the invention.

Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The symbol $\sim\!\!\sim\!\!\sim$, displayed perpendicular to a bond, indicates the point at which the displayed moiety is attached to the remainder of the molecule.

In some embodiments, the definition of terms used herein is according to IUPAC.

The expression "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts). Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative base addition alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of the compound the invention is also within the scope and spirit of the invention. Thus the compound of the invention can be administered to a subject in the form of a pharmaceutically acceptable pro-drug. The term "pro-drug" is used in its broadest sense and encompasses those derivatives that are converted in vivo to the compound of the invention. Such derivatives would readily occur to those skilled in the art. Other texts which generally describe prodrugs (and the preparation thereof) include: Design of Prodrugs, 1985, H. Bundgaard (Elsevier); The Practice of Medicinal Chemistry, 1996, Camille G. Wermuth et al., Chapter 31 (Academic Press); and A Textbook of Drug Design and Development, 1991, Bundgaard et al., Chapter 5, (Harwood Academic Publishers). For example, the N atom on the 1,4-diazinane or piperazine moiety ring may be reacted with an acid (for example acetic acid). An exemplary pharmaceutically acceptable prodrug is a pharmaceutically acceptable ester.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instant description. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38 (1992); Bundgaard, J. Of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology", John Wiley and Sons, Ltd. (2002).

The term "solvate" refers to a physical association of one of the present compounds with one or more solvent molecules. This physical association includes hydrogen bonding. In certain instances, the solvate will be capable of isolation, for example when one or more solvent molecules are incorporated in the crystal lattice of a crystalline solid. "Solvate" encompasses both solution-phase and insoluble solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Class 3 solvents described in the International Conference on Harmonization (ICH), Guide for Industry, Q3C Impurities: Residual Solvents (1997). The compounds as herein described also include each of their solvates and mixtures thereof.

The term "biological sample" as used herein refers any tissue or fluid from a patient that is suitable for detecting a biomarker, such as MDM2 expression status. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the invention, the biological sample comprises blood cells and/or bone marrow cells.

The term "disease" or "condition" denotes disturbances and/or anomalies that as a rule are regarded as being pathological conditions or functions, and that can manifest themselves in the form of particular signs, symptoms, and/or malfunctions. As demonstrated in the examples below, a compound of the invention is an inhibitor of MDM2 protein and can be used in treating diseases and conditions wherein inhibition of MDM2 provides a benefit.

The term "a disease or condition wherein inhibition of MDM2 protein provides a benefit" pertains to a disease or condition in which MDM2 and/or an action of MDM2 is important or necessary, e.g., for the onset, progress, expression of that disease or condition, or a disease or a condition which is known to be treated by a MDM2 inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by MDM2 for any particular cell type, for example, by assays which conveniently can be used to assess the activity of particular compounds.

The term "second therapeutic agent" refers to a therapeutic agent different from a Compound of the invention and that is known to treat the disease or condition of interest. For example when a cancer is the disease or condition of interest, the second therapeutic agent can be a known chemotherapeutic drug, like taxol, or radiation, for example.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a compound of the invention can be administered at the same time or sequentially in any order at different points in time as a second therapeutic agent. A compound of the invention and the second therapeutic agent can be administered separately, in any appropriate form and by any suitable route. When a compound of the invention and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a compound of the invention and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

In various embodiments, the administration of the MDM2 inhibitor of the invention and the second therapeutic agent displays a synergistic effect in treating the disease.

The term "synergistic effect" as used herein refers to action of two or three therapeutic agents such as, for example, a compound of formula (I), and a second MDM2 inhibitor and/or at least one compound operating by a mechanism other than MDM2 inhibition, e.g., a MEK inhibitor compound, e.g., at least one BCL2 inhibitor compound producing an effect, for example, slowing the progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of a drug combination. The corresponding graphs associated with the equations referred to above are the concentration-effect curve, isobologram curve and combination index curve, respectively.

In an exemplary embodiment, the second therapeutic agent is a MEK inhibitor and the MDM2 inhibitor of the invention and the MEK inhibitor are administered concurrently to a subject in need thereof. In an exemplary embodiment, the concurrent coadministration leads to a synergistic effect with respect to treating the disease.

As used herein, the terms "treat," "treating," "treatment," refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce MDM2 signaling in the target cells; and/or relieve, to some extent, one or more of the symptoms associated with the cancer. To the extent the administered compound or composition prevents growth and/or kills existing cancer cells, it may be cytostatic and/or cytotoxic.

In various embodiments, the term "therapeutically effective amount" relates to an amount of compound which, when administered according to a desired dosing regimen, provides the desired therapeutic activity. Dosing may occur at intervals of minutes, hours, days, weeks, months or years or continuously over any one of these periods. Exemplary suitable dosages may lie within the range of about 0.1 ng per kg of body weight to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

In one embodiment, with respect to the treatment of cancer, a therapeutically effective amount refers to the amount of a compound of the invention that (a) decreases the (1) rate of tumor growth; (2) tumor mass; (3) buildup of abnormal cells in tissues and organs; or (4) the number of metastases, in a subject by about 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more; or (b) increases (1) the time to tumor progression; (2) tumor cell apoptosis; or (3) survival time, in a subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more.

Likewise, the term "therapeutic response in a subject" refers to (a) a decrease in the (1) rate of tumor growth; (2) tumor mass; (3) buildup of abnormal cells in tissues and organs; or (4) the number of metastases, in that subject by about 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more; or (b) an increase in (1) the time to tumor progression; (2) tumor cell apoptosis; or (3) survival time, in that subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more.

As used herein, the term "inhibitor" is defined as a compound that binds to and/or inhibits the target MDM2 protein with measurable affinity.

The term "MDM2 inhibitor" or "HDM2 inhibitor" or "Mdm2 inhibitor" as used herein, refer to any compound inhibiting the HDM2/p53 (Mdm2/p53) interaction association. HDM2 (Human homolog of murine double minute 2) is a negative regulator of p53. Mdm2 inhibitors are useful in pharmaceutical compositions for human or veterinary use where inhibition of Mdm2/p53 association is indicated, e.g., in the treatment of tumors and/or cancerous cell growth. In particular, Mdm2 inhibitors are useful in the treatment of human cancer, since the progression of these cancers may be at least partially dependent upon overriding the "gatekeeper" function of p53, for example the overexpression of Mdm2.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "patient or subject" as used herein refers to a mammal. A subject therefore refers to, for example, humans, dogs, cats, horses, cows, pigs, guinea pigs, and the like. Generally, the subject is a human. When the subject is a human, the subject may be either a patient or a healthy human.

The term "proliferative disorder" refers to cells having the capacity for autonomous growth, i.e., an abnormal state of condition characterized by rapidly proliferating cell growth which generally forms a distinct mass that show partial or total lack of structural organization and functional coordination with normal tissue. In various embodiments, the compounds of the invention are used to treat, ameliorate or cure a proliferative disorder.

In some embodiments, the therapeutically effective amount of a compound as defined herein can be administered to a patient alone or admixed with a pharmaceutically acceptable carrier, adjuvant, or vehicle.

The expression "pharmaceutically acceptable carrier, adjuvant, or vehicle" and equivalent expressions, refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester, prodrug, salt of a prodrug, or other derivative of a compound of the present description that, upon administration to a recipient, is capable of providing, either directly or indirectly, a compound of the present description or an inhibitory active metabolite or residue thereof.

III. The Embodiments

The present invention relates to compounds which are binders to MDM2. According to certain embodiments, the compounds are inhibitors of MDM2. In various embodiments, the compounds are in vivo inhibitors of MDM2. The present invention also provides methods of treating disorders by administering to a subject in need thereof a therapeutically effective amount of a MDM2 inhibitor of the invention.

A. The Compounds

The compounds of the present application may be prepared by conventional chemical synthesis, such as exemplified in the Examples appended hereto. As will be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present description. Synthetic chemistry transformations and/or protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The synthesized compounds can be separated from a reaction mixture and further purified by standard methods such as column chromatography, high pressure liquid chromatography, or recrystallization.

The compounds of the present description may be modified by appending various functionalities via any synthetic means delineated herein or otherwise know in the art to enhance selective chemical (e.g. stability) and biological (e.g., affinity for the POI) properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof. As such, the following embodiments are present alone or in combination if applicable.

In various embodiments, the invention provides an inhibitor of MDM2 according to Formula I:

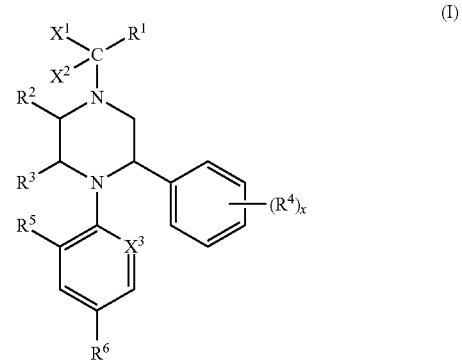

in which $X^1$ and $X^2$ are each H or together are (=O). $R^1$ is selected from substituted or unsubsituted alkyl, substituted or unsubsituted heteroalkyl, substituted or unsubsituted aryl, and substituted or unsubsituted heteroaryl. $R^2$, and $R^3$ are independently selected from H, substituted or unsubsituted alkyl and substituted or unsubsituted heteroalkyl. Each $R^4$ is independently selected from H and halo, with the proviso that at least one of $R^4$ is halo. The index x is an integer selected from 1, 2, 3, 4, and 5. $R^5$ is independently selected from H, substituted or unsubsituted alkyl, substituted or unsubsituted heteroalkyl, amine, and substituted or unsubsituted alkylamine. $R^6$ is selected from halo, haloalkyl, and $CF_3$. $X^3$ is selected from N and $CR^7$ wherein, $R^7$ is selected from H, substituted or unsubsituted alkyl, and substituted or unsubsituted heteroalkyl.

In an exemplary embodiment, $R^4$ is chloro.

In various embodiments, x is 1.

In some embodiments, one of $R^2$ and $R^3$ are independently selected from $C_1$-$C_6$ substituted or unsubstituted straight-chain, branched-chain, and cyclic alkyl moieties, and $C_1$-$C_6$ substituted or unsubstituted straight-chain, branched-chain, and cyclic heteroalkyl moieties.

In various embodiments, $R^5$ is $NH_2$.

In some embodiments, $R^6$ is chloro.

In an exemplary embodiment, $X^3$ is N or CH.

In an exemplary embodiment, $R^1$ is $C_1$-$C_6$ substituted or unsubstituted alkyl.

In various embodiments, $R^1$ is $C_1$-$C_6$ alkyl substituted with a member selected from $C(O)R^{11}$, (=O), and $NR^{12}$, in which $R^{11}$ is selected from H, and substituted or unsubsituted alkyl, substituted or unsubsituted heteroalkyl; and $R^{12}$ is selected from H, substituted or unsubsituted alkyl, and substituted or unsubsituted heteroalkyl.

In various embodiments, $R^1$ comprises a member selected from a substituted or unsubstituted cycloalkyl ring selected from substituted or unsubstituted heterocyclyl, substituted or unsubstituted and substituted or unsubstituted heteroaryl ring.

In some embodiments, $R^1$ comprises a member selected from a substituted or unsubstituted 3-7-member cycloalkyl, substituted or unsubstituted 4-6-member heterocyclyl, substituted or unsubstituted phenyl and substituted or unsubstituted pyridyl.

In an exemplary embodiment, $R^1$ is $C_1$-$C_6$ substituted alkyl; $R^2$, and $R^3$ are independently selected from H, and unsubstituted $C_1$-$C_8$ straight-chain, branched-branched chain and cyclic alkyl; $R^4$ is halo; $R^5$ is independently selected from H, amine and substituted or unsubstituted alkylamine; $R^6$ is selected from halo, and $CF_3$; and $X^3$ is selected from N and CH.

In an exemplary embodiment, one of $R^2$ and $R^3$ is selected from unsubstituted $C_1$-$C_6$ straight-chain, branched-chain, and cyclic alkyl.

In an exemplary embodiment, $R^5$ is $NH_2$.

In an exemplary embodiment, $R^1$ is $C_1$-$C_6$ alkyl substituted with a member selected from $C(O)R^1$ (=O), and $NR^{12}$, in which $R^{11}$ is selected from H, and substituted or unsubstituted alkyl, substituted or unsubsituted heteroalkyl; and $R^{12}$ is selected from H, substituted or unsubsituted alkyl, and substituted or unsubsituted heteroalkyl.

In an exemplary embodiment, the compound of the invention has a structure according to Formula II:

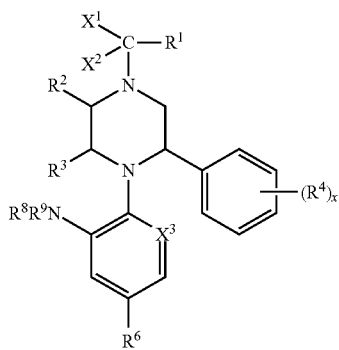

(II)

wherein, $R^8$ and $R^9$ are independently selected from H, acyl, substituted or unsubsituted alkyl, and substituted or unsubsituted heteroalkyl.

In some embodiments, the compound of the invention has a structure according to Formula III:

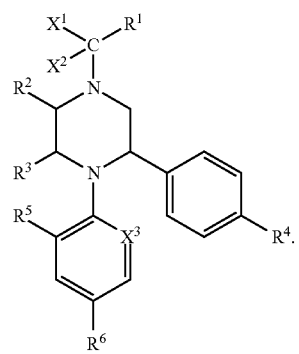

(III)

In various embodiments, the compound of the invention has a structure according to Formula IV:

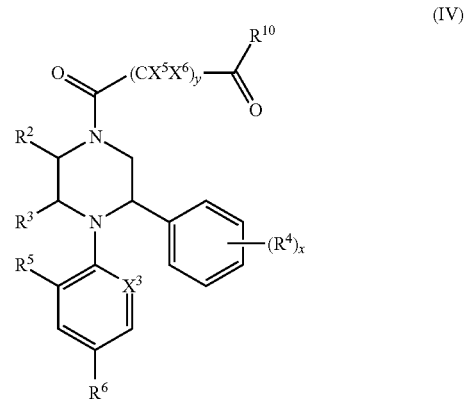

(IV)

in which each $X^5$ and $X^6$ is independently selected from: (i) H, and substituted or unsubstituted alkyl; (ii) one or more pair of $X^5$ and $X^6$, together with the carbon to which they are each bound, are (C=O); (iii) $X^5$ and $X^6$, together with the carbon atoms to which they are bound, are joined to form a 3-, 4-, 5-, or 6-member ring, selected from substituted or unsubstituted cycloalkyl, substituted or unsubstituted aryl, substituted or unsubstituted heterocycloalkyl, and substituted or unsubstituted heteroaryl; and (iv) a combination thereof. The index y is 1, 2, 3, 4, 5, or 6. $R^{10}$ is selected from $OR^{13}$, $NR^{13}R^{14}$, wherein $R^{13}$ and $R^{14}$ are independently selected from H, substituted or unsubstituted alkyl and substituted or unsubstituted heteroalkyl, and $R^{13}$ and $R^H$, together with the nitrogen to which they are bound, are optionally joined to form a ring of 4, 5 or 6 members, which is selected from substituted or unsubstituted cycloalkyl, substituted or unsubstituted heterocycloalkyl, substituted or unsubstituted aryl and substituted or unsubstituted heteroaryl.

In various embodiments, the compound of the invention has a structure according to Formula V:

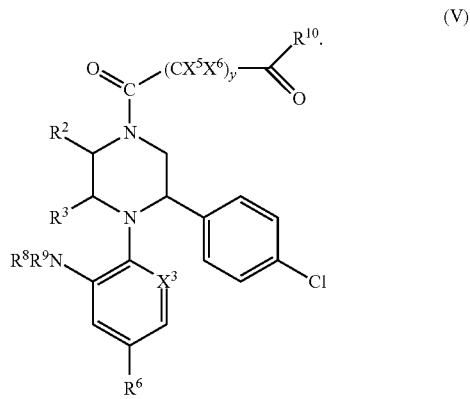

(V)

In an exemplary embodiment, the compound of the invention has a structure according to Formula VI:

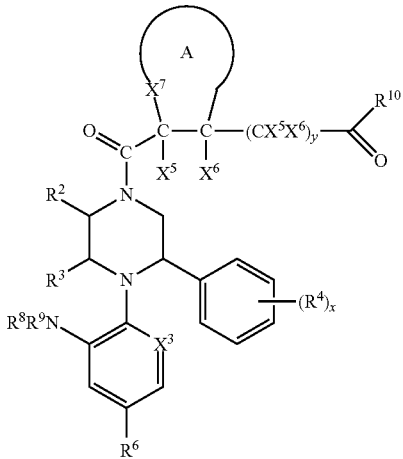
(VI)

wherein, ring A is selected from a 3-, 4-, 5-, or 6-member ring, selected from substituted or unsubstituted cycloalkyl, substituted or unsubstituted aryl, substituted or unsubstituted heterocycloalkyl, and substituted or unsubstituted heteroaryl.

In various embodiments, $R^7$ is H.

In various embodiments, $X^3$ is N.

In some embodiments, the compound of the invention is of the formula:

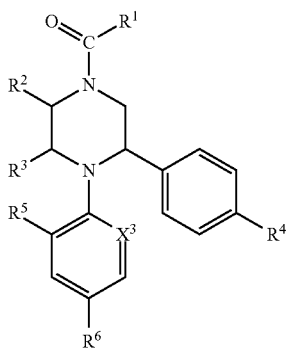

In an exemplary embodiment, the compound of the invention is of the formula:

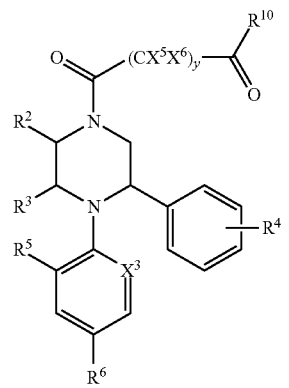

wherein, each $X^5$ and $X^6$ is independently selected from: (i) H, and substituted or unsubstituted alkyl; and (ii) one or more pair of $X^5$ and $X^6$, together with the carbon to which they are each bound, are (C=O); y is 1, 2, 3, 4, 5, or 6; $R^{10}$ is selected from $OR^{13}$, $NR^{13}R^{14}$ wherein, $R^{13}$ and $R^{14}$ are independently selected from H, substituted or unsubstituted alkyl and substituted or unsubstituted heteroalkyl, and $R^{13}$ and $R^{14}$, together with the nitrogen to which they are bound, are optionally joined to form a ring of 4, 5 or 6 members, which is selected from substituted or unsubstituted cycloalkyl, substituted or unsubstituted heterocycloalkyl, substituted or unsubstituted aryl and substituted or unsubstituted heteroaryl.

In various embodiments, the compound of the invention is of the formula:

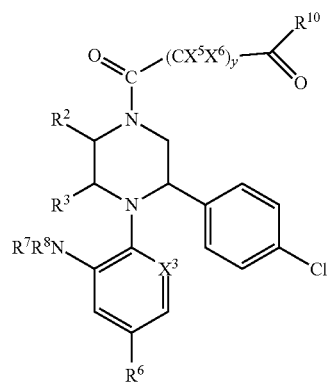

In some embodiments, $R^1$ comprises:

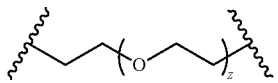

wherein z is an integer selected from 1, 2, 3, 4, 5, and 6.

In some embodiments, the compound the invention is selected from the following compounds in Table 1:

TABLE 1

Compound identification and chemical structures of selected MDM2 binders.

| Compound ID. | Structure |
|---|---|
| 1 | 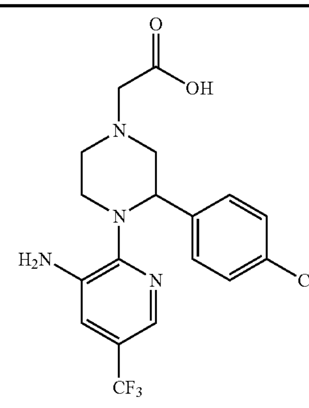 |

TABLE 1-continued
Compound identification and chemical structures of selected MDM2 binders.
| Compound ID. | Structure |
|---|---|
| 2 | 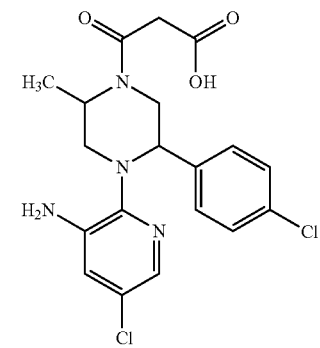 |
| 3 | 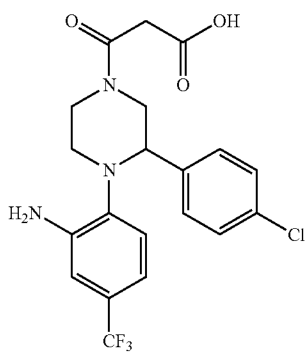 [SMILES: Nc1cc(C(F)(F)F)ccc1N1CCN(C(=O)CC(=O)O)CC1c1ccc(Cl)cc1] |
| 4 | 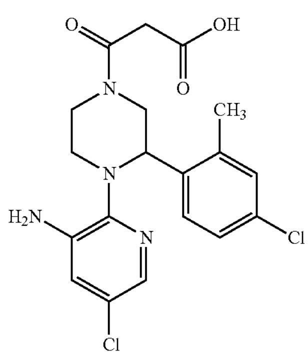 [SMILES: Cc1cc(Cl)ccc1C1CN(C(=O)CC(=O)O)CCN1c1ncc(Cl)cc1N] |
| 5 | 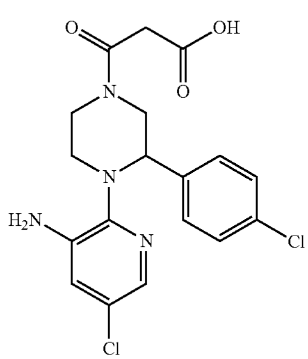 [SMILES: Nc1cc(Cl)cnc1N1CCN(C(=O)CC(=O)O)CC1c1ccc(Cl)cc1] |
| 6 | 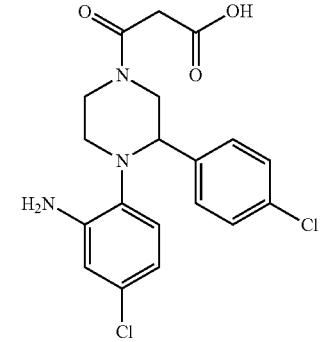 [SMILES: Nc1cc(Cl)ccc1N1CCN(C(=O)CC(=O)O)CC1c1ccc(Cl)cc1] |
| 7 | |
| 8 | |
| 9 | |

TABLE 1-continued
Compound identification and chemical structures of selected MDM2 binders.
| Compound ID. | Structure |
|---|---|
| 10 | 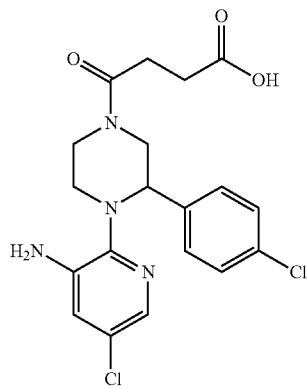 [SMILES: Nc1cc(Cl)cnc1N1CCN(C(=O)CCC(=O)O)CC1c1ccc(Cl)cc1] |
| 11 | 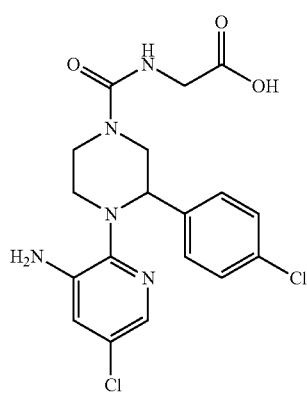 [SMILES: Nc1cc(Cl)cnc1N1CCN(C(=O)NCC(=O)O)CC1c1ccc(Cl)cc1] |
| 12 | 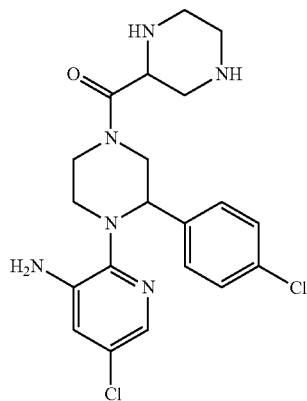 [SMILES: Nc1cc(Cl)cnc1N1CCN(C(=O)C2CNCCN2)CC1c1ccc(Cl)cc1] |
| 13 | 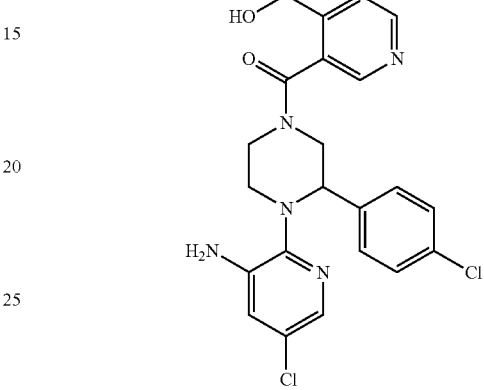 |
| 14 | 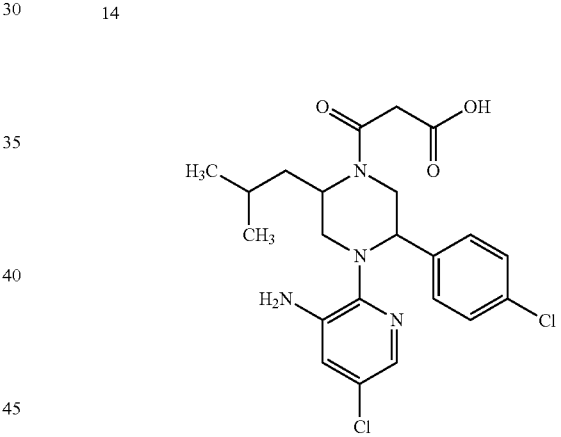 |
| 15 | 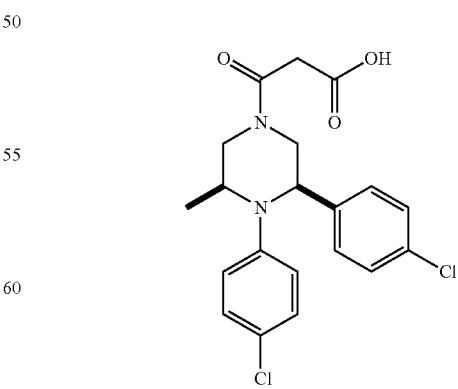<br>(cis racemic) |

TABLE 1-continued

Compound identification and
chemical structures of selected MDM2 binders.

| Compound ID. | Structure |
|---|---|
| 16 | (cis racemic) |
| 17 | 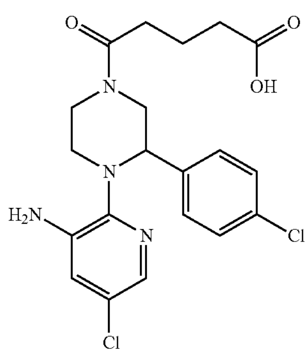 [SMILES: Nc1cc(Cl)cnc1N1CCN(C(=O)CCCC(=O)O)CC1c1ccc(Cl)cc1] |
| 18 | 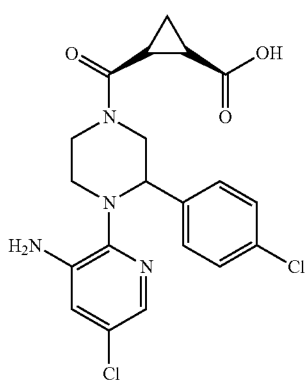 |
| 19 | 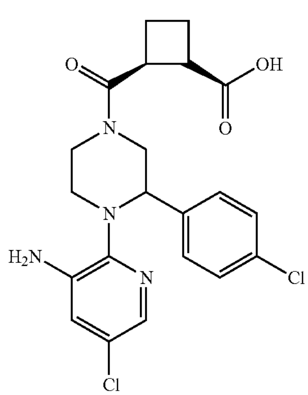 |
| 20 | (cis racemic) |
| 21 | (cis racemic) |
| 22 | |
| 23 | |

TABLE 1-continued
Compound identification and chemical structures of selected MDM2 binders.
| Compound ID. | Structure |
|---|---|
| 24 | 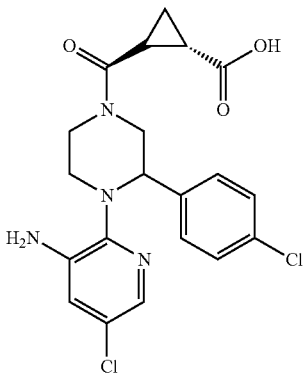 |
| 25 | 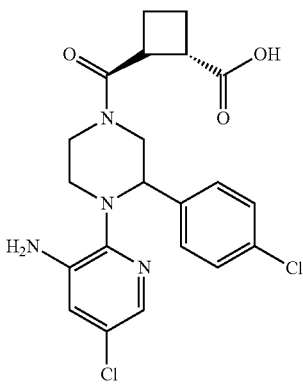 |
| 26 | 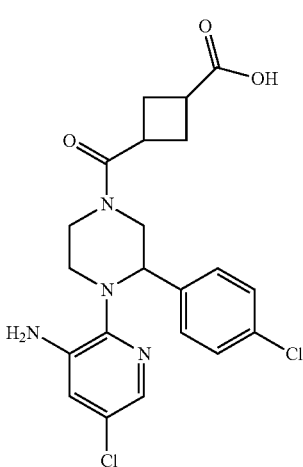 [SMILES: Nc1cc(Cl)cnc1N1CCN(C(=O)C2CC(C(=O)O)C2)CC1c1ccc(Cl)cc1] |
| 27 | 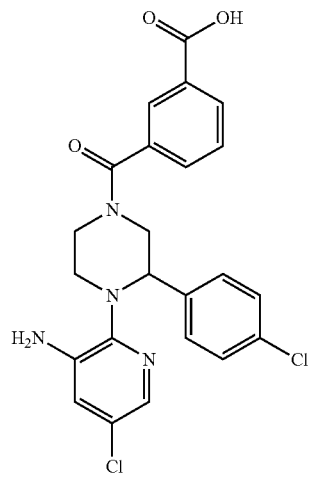 [SMILES: Nc1cc(Cl)cnc1N1CCN(C(=O)c2cccc(C(=O)O)c2)CC1c1ccc(Cl)cc1] |
| 28 | 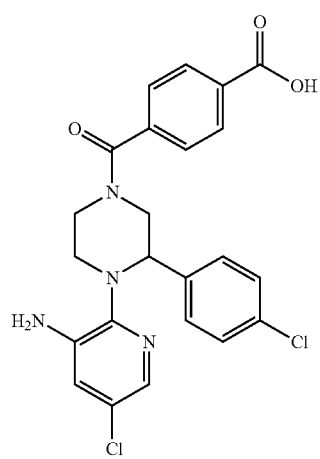 [SMILES: Nc1cc(Cl)cnc1N1CCN(C(=O)c2ccc(C(=O)O)cc2)CC1c1ccc(Cl)cc1] |
| 29 | 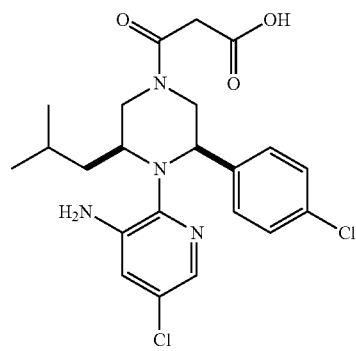<br>(cis racemic) |

TABLE 1-continued

Compound identification and chemical structures of selected MDM2 binders.

| Compound ID. | Structure |
|---|---|
| 30 | 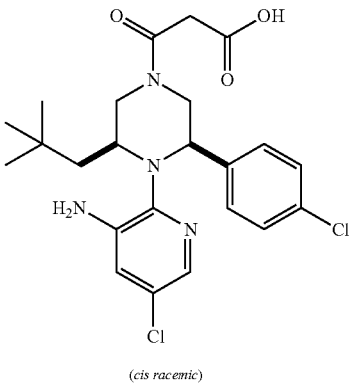 [SMILES: CC(C)(C)C[C@H]1CN(C(=O)CC(=O)O)C[C@@H](c2ccc(Cl)cc2)N1c1ncc(Cl)cc1N]<br>(cis racemic) |
| 31 | 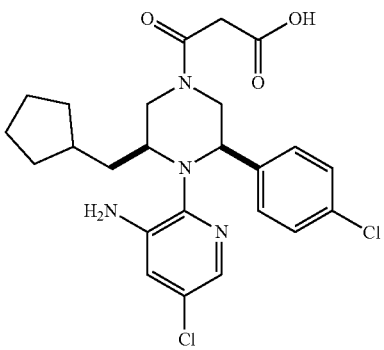<br>(cis racemic) |

The compound of the invention may be in amorphous or crystalline form either as the free compound or as a solvate (e.g. hydrate) and it is intended that both forms are within the scope of the present invention. Methods of solvation are generally known within the art.

Advantageously, the exemplary compounds of the invention are able to permeate cells to exert their effect, and accordingly have good cellular activity.

In another aspect, the present invention relates to a pharmaceutical composition comprising an effective amount of compound set forth in a Formula herein or a pharmaceutically acceptable salt, solvate, stereoisomer or prodrug thereof. The pharmaceutical composition may optionally be in combination with a pharmaceutically acceptable carrier, excipient or diluent.

B. The Methods

In various embodiments, the present invention relates to a method of inducing inhibition of an overexpressed protein in a cell, including a step of contacting a compound set forth in a Formula herein with the cell to induce degradation of the overexpressed protein in the cell.

In various embodiments, the present invention provides a method of treating a disease or condition associated with an overexpressed protein, comprising administering a compound of a Formula set forth herein or a pharmaceutically acceptable salt, solvate, stereoisomer or prodrug thereof in a subject in need thereof.

In various embodiments, the present invention provides a compound of a Formula set forth herein or a pharmaceutically acceptable salt, solvate, stereoisomer or prodrug thereof for use as a medicament.

In various embodiments, the invention provides a compound of Formula (I) or a pharmaceutically acceptable salt, solvate, stereoisomer or prodrug thereof for use in the treatment of a disease or condition associated with an overexpressed protein.

In an exemplary embodiment, the provides a use of a compound of the invention or a pharmaceutically acceptable salt, solvate, stereoisomer or prodrug thereof in the manufacture of a medicament for the treatment of a disease or condition associated with an overexpressed protein.

In various embodiments, the invention provides a method of inhibiting MDM2 in a biological sample, the method including contacting the sample with a compound of the invention.

In an exemplary embodiment, the invention provides a method of treating a MDM2-mediated disorder, disease, or condition in a patient comprising administering to said patient the pharmaceutical formulation of the invention.

In an exemplary embodiment, the invention provides a method of treating a MDM2-mediated disorder wherein the disorder is selected from an autoimmune disorder, an inflammatory disorder, a proliferative disorder, an endocrine disorder, a neurological disorder, or a disorder associated with transplantation. The method includes administering to a subject having the disorder a therapeutically effective amount of a compound of the invention. In various embodiments, the proliferative disorder is cancer.

The compound of the invention can be administered to a subject as a pharmaceutically acceptable salt thereof.

The compound of the invention, or a pharmaceutically acceptable salt, solvate or prodrug thereof is administered to the patient in a therapeutically effective amount.

Suitable dosage amounts and dosing regimens can be determined by the attending physician and may depend on the severity of the condition as well as the general age, health and weight of the patient to be treated.

Exemplary unit dosage composition or combinations are those containing a daily dose or unit, daily sub-dose, as herein above described, or an appropriate fraction thereof, of the active ingredient.

The compound of the invention may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

An exemplary carrier is pharmaceutically "acceptable" in the sense of being compatible with the other ingredients of the composition and not injurious to the patient. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Exemplary compounds, compositions or combinations of the invention formulated for intravenous, intramuscular or intraperitoneal administration, and a compound of the invention or a pharmaceutically acceptable salt, solvate or prodrug thereof may be administered by injection or infusion.

Injectables for such use can be prepared in conventional forms, either as a liquid solution or suspension or in a solid form suitable for preparation as a solution or suspension in a liquid prior to injection, or as an emulsion. Carriers can include, for example, water, saline (e.g., normal saline (NS), phosphate-buffered saline (PBS), balanced saline solution (BSS)), sodium lactate Ringer's solution, dextrose, glycerol, ethanol, and the like; and if desired, minor amounts of auxiliary substances, such as wetting or emulsifying agents, buffers, and the like can be added. Proper fluidity can be maintained, for example, by using a coating such as lecithin, by maintaining the required particle size in the case of dispersion and by using surfactants.

The compound, composition or combinations of the invention may also be suitable for oral administration and may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. In another embodiment, the compound of formula (I) or a pharmaceutically acceptable salt, solvate or prodrug is orally administrable.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The compound, composition or combinations of the invention may be suitable for topical administration in the mouth including lozenges comprising the active ingredient in a flavored base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

The compound, composition or combinations of the invention may be suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

The compound, composition or combination of the invention may be suitable for parenteral administration include aqueous and non-aqueous isotonic sterile injection solutions which may contain anti-oxidants, buffers, bactericides and solutes which render the compound, composition or combination isotonic with the blood of the intended recipient; and aqueous and non-aqueous sterile suspensions which may include suspending agents and thickening agents. The compound, composition or combination may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the active ingredients particularly mentioned above, the composition or combination of this invention may include other agents conventional in the art having regard to the type of composition or combination in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

In another embodiment, present invention provides methods of treating a subject having cancer, comprising (a) determining whether a biomarker is present or absent in a biological sample taken from the subject; and (b) administering a therapeutically effective amount of a compound of the invention to the subject if the biomarker is present in the biological sample. See, e.g., Goossens et al., Transl Cancer Res. 4:256-269 (2015); Kamel and Al-Amodi, Genomics Proteomics Bioinformatics 15:220-235 (2017); and Konikova and Kusenda, Neoplasma 50:31-40 (2003).

The term "biomarker" as used herein refers to any biological compound, such as a gene, a protein, a fragment of a protein, a peptide, a polypeptide, a nucleic acid, etc., that can be detected and/or quantified in a cancer patient in vivo or in a biological sample obtained from a cancer patient. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration, i.e., expression level, of the biomarker in a cancer patient, or biological sample obtained from the cancer patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

Biomarkers include, but are not limited to, MDM2, p53 and any one or more of the other biomarkers disclosed in US 2015/0301058. In one embodiment, the measurable aspect of the biomarker is its expression status. In one embodiment, the measurable aspect of the biomarker is its mutation status.

In one embodiment, the biomarker is MDM2 which is differentially present in a subject of one phenotypic status, e.g., a subject having a hematological cancer, as compared with another phenotypic status, e.g., a normal undiseased subject or a patient having cancer without overexpression MDM2. In one embodiment, the biomarker is overexpression of MDM2.

Biomarker standards can be predetermined, determined concurrently, or determined after a biological sample is obtained from the subject. Biomarker standards for use with the methods described herein can, for example, include data from samples from subjects without cancer; data from samples from subjects with cancer, e.g., breast cancer, that is not metastatic; and data from samples from subjects with cancer, e.g., breast cancer, that metastatic. Comparisons can be made to establish predetermined threshold biomarker standards for different classes of subjects, e.g., diseased vs. non-diseased subjects. The standards can be run in the same assay or can be known standards from a previous assay.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

In addition to individual biological compounds, e.g., MDM2, the term "biomarker" as used herein is meant to include groups, sets, or arrays of multiple biological compounds. For example, the combination of MDM2 and p53 may comprise a biomarker. The term "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting MDM2 expression, or the expression or mutation levels of any other biomarker in a patient or a biological sample may be used in the methods of the invention. Examples include, but are not limited to, PCR (polymerase chain reaction), or RT-PCR, flow cytometry, Northern blot, Western blot, ELISA (enzyme linked immunosorbent assay), RIA (radioimmunoassay), gene chip analysis of RNA expression, immunohistochemistry or immunofluorescence, pyrosequencing, ion torrent, and sequence by synthesis. See, e.g., Slagle et al. Cancer 83:1401 (1998). Certain embodiments of the invention include methods wherein biomarker RNA expression (transcription) is determined. Other embodiments of the invention include methods wherein protein expression in the biological sample is determined. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995); Kamel and Al-Amodi, Genomics Proteomics Bioinformatics 15:220-235 (2017). For northern blot or RT-PCR analysis, RNA is isolated from the tumor tissue sample using RNAse free techniques. Such techniques are commonly known in the art.

In one embodiment of the invention, a biological sample is obtained from the patient and the biological sample is assayed for determination of a biomarker, e.g., MDM2, expression or mutation status. In one embodiment, flow cytometry is used to determine MDM2 expression.

In another embodiment of the invention, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is prehybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabled probes and their use are well known in the art. The presence and or relative levels of expression of the biomarker being assayed can be quantified using, for example, densitometry.

In another embodiment, biomarker expression and/or mutation status is determined using RT-PCR. RT-PCR allows detection of the progress of a PCR amplification of a target gene in real time. Design of the primers and probes required to detect expression and/or mutation status of a biomarker of the invention is within the skill of a practitioner of ordinary skill in the art. RT-PCR can be used to determine the level of RNA encoding a biomarker of the invention in a tumor tissue sample. In an embodiment of the invention, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., Cold Spring Harbor Symp. Quant. Biol. 51:263 (1986); EP 50,424; EP 84,796; EP 258,017; EP 237,362; EP 201,184; U.S. Pat. Nos. 4,683,202; 4,582,788; 4,683,194.

In some embodiments, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In various embodiments, the expression of a protein encoded by a biomarker is detected by enzyme-linked immunosorbent assay (ELISA). In one embodiment, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In some embodiments, the expression of a biomarker is evaluated by use of a gene chip or microarray. Such techniques are within ordinary skill held in the art.

The invention provides the following particular embodiments in connection with biomarkers.

Embodiment I. A method of treating a subject having cancer, the method comprising: (a) determining the amount of expression, e.g., overexpression, in a biological sample taken from the subject; and (b) administering a therapeutically effective amount of a compound of the invention to the subject following determining the amount of expression of MDM2 in the biological sample.

Embodiment II. A method of identifying whether a subject having cancer as a candidate for treatment with a compound of the invention, the method comprising: (a) determining the amount of expression, e.g., overexpression, of MDM2 in a biological sample taken from the subject; and (b) identifying the subject as being a candidate for treatment if an overexpression of MDM2 is present; or (c) identifying the subject as not being a candidate for treatment if an overexpression of MDM2 is absent.

Embodiment III. A method of predicting treatment outcome in a subject having cancer, the method comprising determining the amount of expression, e.g., overexpression of MDM2 in a biological sample taken from the subject, wherein: (a) the presence of an overexpression of MDM2 in the biological sample indicates that administering a compound of the invention to the subject will produce a therapeutic response in the subject; and (b) the absence of an overexpression of MDM2 in the biological sample indicates that administering compound of the invention to the subject will not produce a therapeutic response in the subject.

Embodiment IV. A method, comprising administering a therapeutically effective amount of compound of the invention to a subject in need thereof, wherein: (a) the subject has cancer; and (b) the patient displays an overexpression of MDM2.

It will be appreciated that many further modifications and permutations of various aspects of the described embodiments are possible. Accordingly, the described aspects are intended to embrace all such alterations, modifications, and variations that fall within the spirit and scope of the appended statements.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1

Identification of the Inhibitors

Using biophysical fragment screening techniques, fragments were identified which bind to MDM2. For example, protein NMR studies and thermal shift assays were performed to analyse the fragments binding to MDM2, These fragments were then further modified and optimized to generate more potent MDM2 binders"

Example 2

Synthesis and Characterization of MDM2 Inhibitors
General Procedures for the Synthesis of N-(Hetero)Aryl Piperazine Scaffolds:
Procedure I:

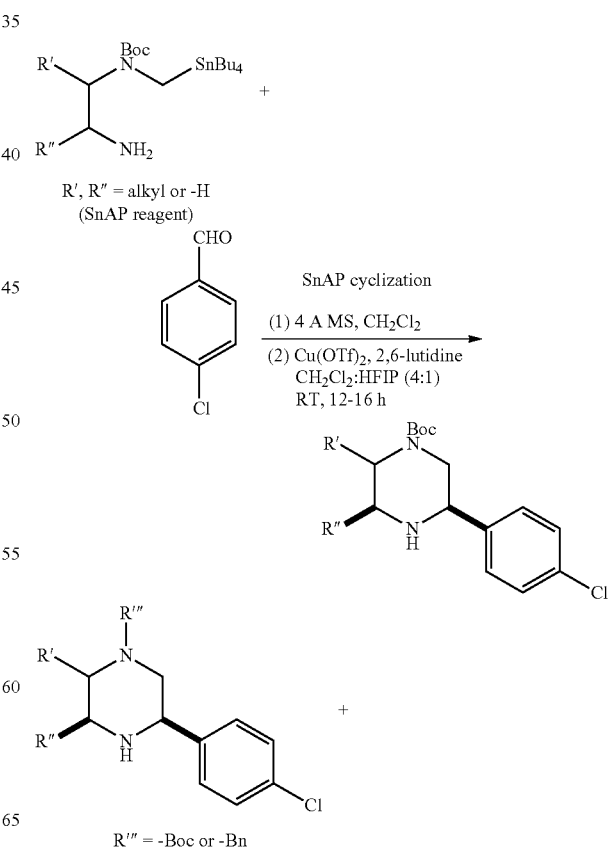

-continued

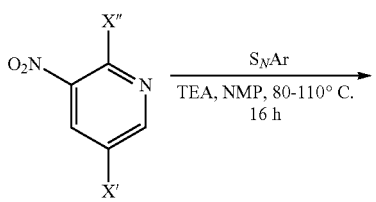

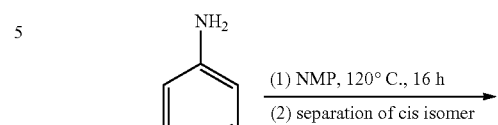

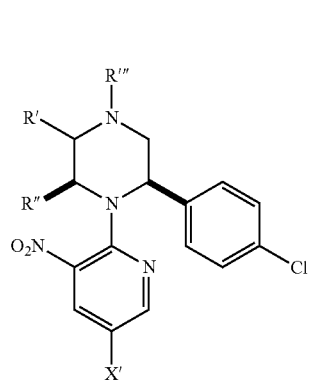

X″ = -F or -Cl
X′ = -CF₃ or -Cl

The SnAP (Stannyl Amine Protocol) reagent (1.0 equiv.) was treated with 4-chlorobenzaldehye (1.0 equiv.) in anhydrous $CH_2Cl_2$ in the presence of 4 Å molecular sieves. The reaction mixture was stirred for two hours and filtered through a short layer of celite. The resulting solution was concentrated in vacuo to afford the imine. Separately, a mixture of anhydrous $Cu(OTf)_2$ (1.0 equiv.) and 2,6-lutidine (2-3 equiv.) were suspended in a 4:1 mixture of $CH_2Cl_2$:HFIP and stirred at room temperature for 1 h. The imine (1.0 equiv.) was added to this suspension and further stirred for 12-16 h. The reaction mixture was concentrated in vacuo and purified using flash column chromatography to afford the piperazine as the desired racemic cis isomer over 30% yield.

Mono N-Boc or N-Bn protected piperazine (1.0 equiv.) was added to a solution of anhydrous triethylamine (3.0 equiv.) and 2-halopyridine (3.0 equiv. added in two batches) in anhydrous NMP and heated at 80-110° C. for 12 h. The resulting mixture was filtered through celite and purified by flash column chromatography to afford the desired N-(hetero)aryl piperazine in 10-14% yield.

Procedure II:

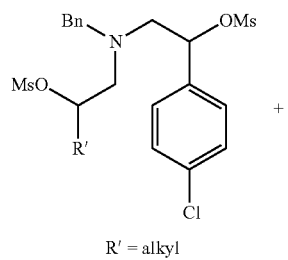

R′ = alkyl 2-(benzyl(2-((methylsulfonyl)oxy)alkyl)amino)-1-(4-chlorophenyl)ethyl methanesulfonate (1.0 equiv.) and 4-chloroaniline (1.0 equiv.) were dissolved in NMP. The reaction was heated at 120° C. for 16 h. After completion of the reaction, the solvent was evaporated in vacuo and subjected to flash column chromatography to isolate the racemic cis isomer from the crude isomeric mixture in 5-20% yield. The product was further characterized by 2D-NMR spectroscopy.

2.1a General Procedure for Ester Hydrolysis (Procedure A):

To a solution of ester (1.0 equiv.) in a mixture of THF and $H_2O$ (2:1) or EtOH and $H_2O$ (2:1) was added $LiOH \cdot H_2O$ (2.0-3.0 equiv.) The mixture was stirred at room temperature for 1-16 h. After completion of starting material, the reaction mixture was concentrated under vacuum. Water was added to the residue and the pH was adjusted to 2-7 using 1 N HCl. The aqueous layer was extracted with ethyl acetate (x 3). The combined organic layers were washed with brine, dried with $Na_2SO_4$, filtered, and concentrated under vacuum. The residue was further purified by prep-HPLC to afford the desired acid.

2.1b General procedure for de-protection of N-Boc group (Procedure B):

4N HCl in 1,4-dioxane (0.25-0.5 mL) was added to the N-Boc intermediate (0.018-0.25 mmol). The solution was stirred for 0.5-2 h at room temperature. After completion of the reaction, the reaction mixture was concentrated under vacuum to afford the N-Boc deprotected product.

2.1c General procedure for reduction of nitro group (Procedure C):

To a solution of nitro compound (1.0 equiv.) in 1,4-dioxane and $H_2O$ (4:1) was added zinc powder (8.0 equiv.) and $NH_4Cl$ (8.0 equiv.). The reaction mixture was stirred at 50° C. for 12 h. After completion of starting material, the reaction mixture was filtered, and the filtrate was concentrated under vacuum. The resulting mixture was purified by prep-HPLC to afford the purified product.

2.2 Synthesis of 2-(4-(3-amino-5-(trifluoromethyl)pyridin-2-yl)-3-(4-chlorophenyl)piperazin-1-yl)acetic acid (Compound 1)

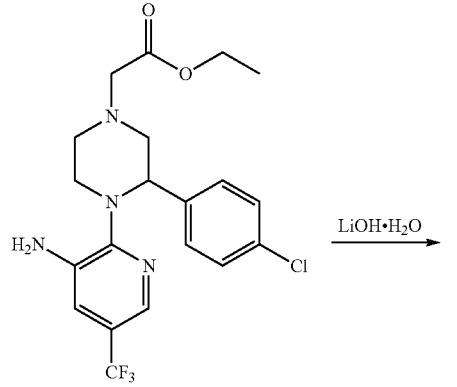

Compound 1 was prepared according to the general procedure A. Yield: 41.60% yield, (97.42% purity). $^1$H NMR (400 MHz, DMSO-$d_6$) 7.66 (s, 1H), 7.33-7.27 (m, 2H), 7.24-7.18 (m, 2H), 7.13 (d, J=2.0 Hz, 1H), 5.58 (br s, 2H), 4.65-4.58 (m, 1H), 3.28-3.25 (m, 1H), 3.21 (d, J=9.6 Hz, 2H), 2.92 (d, J=9.2 Hz, 2H), 2.80-2.71 (m, 1H), 2.64-2.59 (m, 1H), 2.43-2.38 (m, 1H). LC-MS: $t_R$=1.597 min (10-80CD_7min_220&254), m/z=415.1 [M+H]$^+$.

2.3 Synthesis of 2-(4-(3-acetamido-5-(trifluoromethyl)pyridin-2-yl)-3-(4-chlorophenyl)piperazin-1-yl)acetic acid (Compound 2)

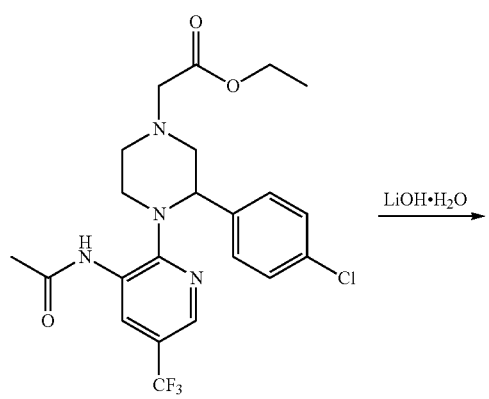

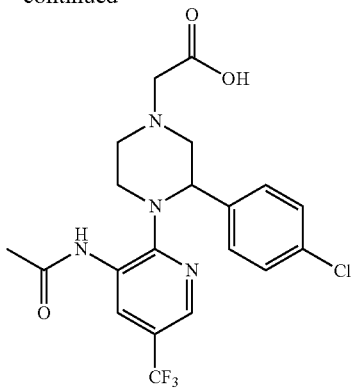

Compound 2 was prepared according to the general procedure A. Yield: 85% yield, (98.33% purity). $^1$H NMR (400 MHz, CDCl$_3$) 8.85 (s, 1H), 8.31 (s, 1H), 8.22 (d, J=1.2 Hz, 1H), 7.17 (s, 4H), 4.80 (dd, J=2.8, 10.4 Hz, 1H), 3.45 (s, 2H), 3.27 (d, J=10.8 Hz, 1H), 3.24-3.10 (m, 3H), 3.07 (d, J=9.2 Hz, 1H), 2.93 (t, J=10.8 Hz, 1H), 2.31 (s, 3H). LC-MS: $t_R$=1.783 min (10 80CD_7min_220&254), m/z=457.1 [M+H]$^+$.

2.4 Synthesis of 3-(4-(2-amino-4-(trifluoromethyl)phenyl)-3-(4-chlorophenyl)piperazin-1-yl)-3-oxopropanoic acid (Compound 3)

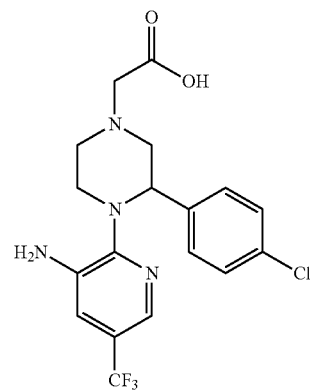

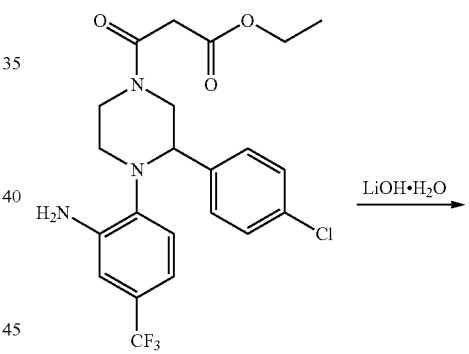

Compound 3 was prepared according to the general procedure A. Yield: 40.16% (98.89% purity). $^1$H NMR (400 MHz, CDCl$_3$) 7.26-7.12 (m, 4H), 6.92-6.82 (m, 2H), 6.81-6.74 (m, 1H), 4.79-4.68 (m, 1H), 4.25-4.16 (m, 1H), 3.94-3.77 (m, 1H), 3.62-3.43 (m, 2H), 3.43-3.22 (m, 2H), 3.19-2.80 (m, 1H), 2.73-2.59 (m, 1H). LC-MS: $t_R$=3.465 min (10-80AB_7min_220&254), m/z=441.8 [M+H]$^+$.

2.5 Synthesis of 3-(4-(3-amino-5-chloropyridin-2-yl)-3-(4-chloro-2-methylphenyl)piperazin-1-yl)-3-oxopropanoic acid (Compound 4)

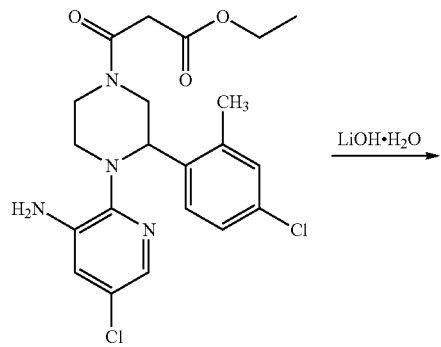

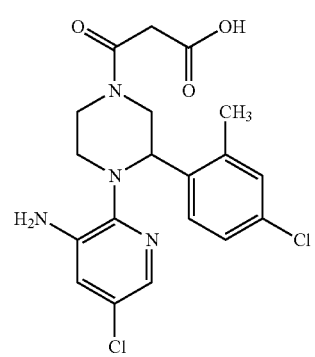

Compound 4 was prepared according to the general procedure A. Yield: 13.44% (96.56% purity). $^1$H NMR (400 MHz, CDCl$_3$) 7.56-7.51 (m, 1H), 7.24-7.15 (m, 1H), 7.10-7.04 (m, 1H), 7.02-6.94 (m, 1H), 6.87 (s, 1H), 4.80-4.60 (m, 2H), 3.95-3.86 (m, 0.5H), 3.78-3.67 (m, 0.5H), 3.71-3.47 (m, 2.5H), 3.46-3.23 (m, 2H), 2.85-2.67 (m, 1.5H), 2.44 (d, J=2.8 Hz, 3H). LC-MS: $t_R$=3.472 min (10-80AB_7min_220&254), m/z=423.0 [M+H]$^+$.

2.6 Synthesis of 3-(4-(3-amino-5-chloropyridin-2-yl)-3-(4-chloro-2-methylphenyl)piperazin-1-yl)-3-oxopropanoic acid (Compound 5)

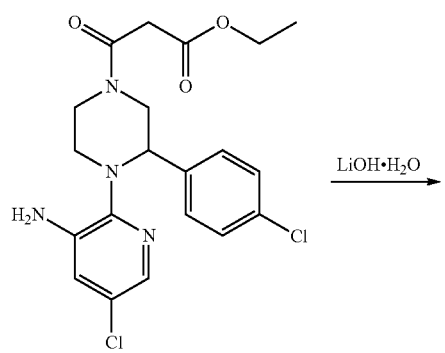

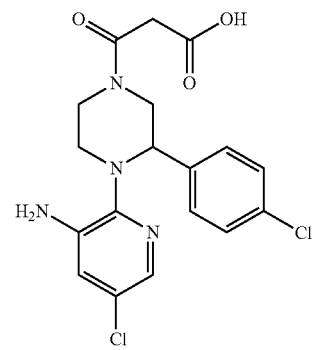

Compound 5 was prepared according to the general procedure A. Yield: 23.67% (purity 97.46%). $^1$H NMR (400 MHz, CDCl$_3$) 7.41 (s, 1H), 7.17-6.95 (m, 4H), 6.76 (d, J=14.4 Hz, 1H), 4.47-4.38 (m, 1H), 4.37-4.17 (m, 2H), 3.99-3.71 (m, 1H), 3.44-3.23 (m, 2H), 3.09-2.85 (m, 1H), 2.68-2.51 (m, 2H). LC-MS: $t_R$=2.908 min (10-80AB_7min_220&254), m/z=408.7 [M+H]$^+$.

2.7 Synthesis of 3-(4-(3-amino-5-chloropyridin-2-yl)-5-(4-chlorophenyl)-2-methylpiperazin-1-yl)-3-oxopropanoic acid (Compound 6)

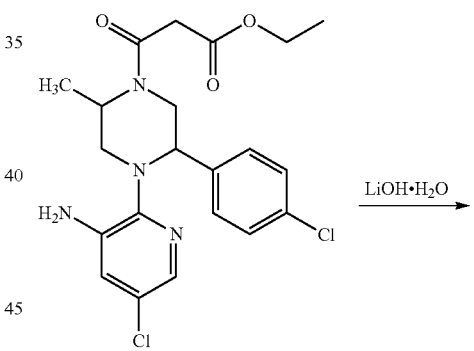

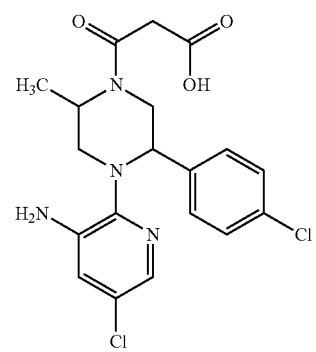

Compound 6 was prepared according to the general procedure A. Yield: 65.75% (100% purity). $^1$H NMR (400 MHz, CDCl$_3$) 7.56-7.54 (m, 1H), 7.26-7.16 (m, 4H), 6.90-6.88 (m, 1H), 5.02-4.46 (m, 2H), 4.20-3.63 (m, 1H), 3.50-2.90 (m, 5H), 1.69-1.55 (m, 3H). LC-MS: $t_R$=3.199 min (10-80AB_7min_220&254), m/z=423.0 [M+H]$^+$.

2.8 Synthesis of 3-(4-(2-amino-4-chlorophenyl)-3-(4-chlorophenyl)piperazin-1-yl)-3-oxopropanoic acid (Compound 7)

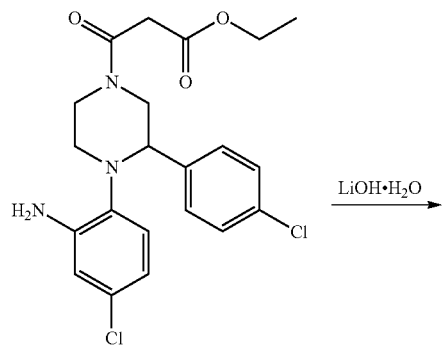

Compound 7 was prepared according to the general procedure A. Yield: 29.68% (97.89% purity). ¹H NMR (400 MHz, CDCl₃) 7.25-7.11 (m, 4H), 6.71 (dd, J=2.8, 8.8 Hz, 1H), 6.63 (s, 1H), 6.52-6.46 (m, 1H), 4.80-4.65 (m, 1H), 4.17-4.07 (m, 1H), 3.92-3.74 (m, 1H), 3.59-3.44 (m, 2H), 3.41-3.18 (m, 2H), 3.15-2.76 (m, 1H), 2.73-2.59 (m, 1H). LC-MS: $t_R$=3.181 min (10-80AB_7min_220&254), m/z=407.7 [M+H]⁺.

2.9 Synthesis of 3-(4-(3-amino-5-chloropyridin-2-yl)-5-(4-chlorophenyl)-2-isopropylpiperazin-1-yl)-3-oxopropanoic acid (Compound 8)

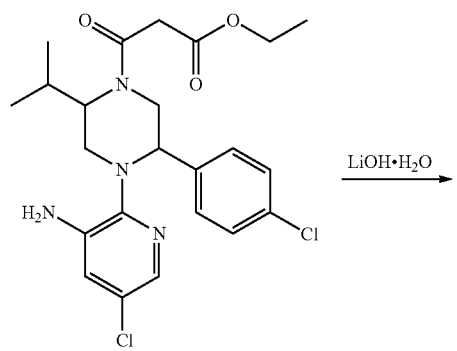

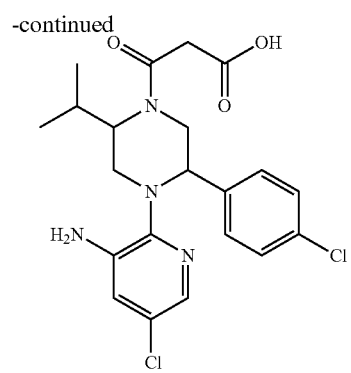

Compound 8 was prepared according to the general procedure A. Yield: 53.11% (100% purity). ¹H NMR (400 MHz, DMSO-d₆) 7.45-7.28 (m, 3H), 7.27-7.15 (m, 2H), 6.99-6.92 (m, 1H), 5.37 (br s, 2H), 4.53-4.33 (m, 1H), 4.29-4.15 (m, 1H), 3.82-3.66 (m, 2H), 3.17-3.12 (m, 1H), 3.08-3.02 (m, 1H), 2.94-2.89 (m, 0.4H), 2.82-2.73 (m, 0.6H), 2.67-2.56 (m, 1H), 2.42-2.40 (m, 0.4H), 2.03-1.94 (m, 0.6H), 1.12-1.03 (m, 3H), 0.86-0.80 (m, 3H). LC-MS: $t_R$=3.598 min (10-80AB_7min_220&254), m/z=450.9 [M+H]+.

2.13 Synthesis of 1-(4-(3-amino-5-chloropyridin-2-yl)-3-(4-chlorophenyl)piperazin-1-yl)-2-(piperazin-1-yl)ethenone (Compound 9)

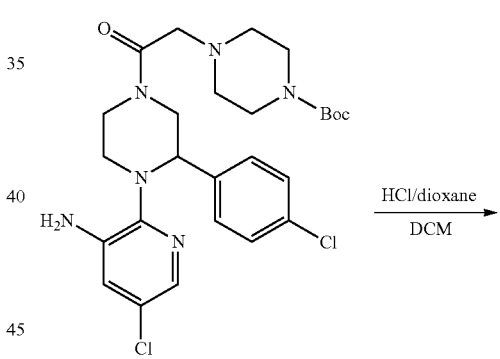

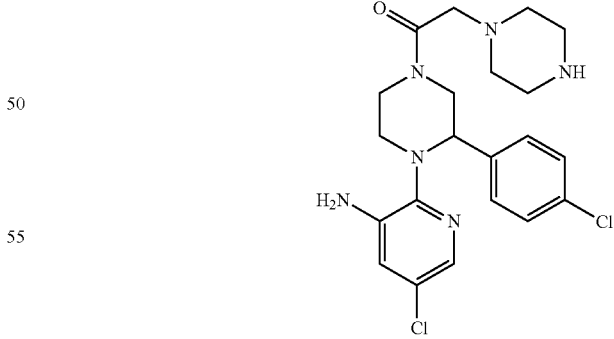

Compound 9 was prepared according to the general procedure B. Yield: 48.19% (98.54% purity). ¹H NMR (400 MHz, DMSO-d₆) 9.77 (s, 2H), 7.40 (d, J=8.4 Hz, 1H), 7.34-7.24 (m, 4H), 6.94-6.91 (m, 1H), 4.70-4.26 (m, 5H), 3.82-3.60 (m, 5H), 3.25-3.02 (m, 5H), 2.91-2.80 (m, 1H), 2.72-2.60 (m, 1H). LC-MS: $t_R$=4.400 min (10-80CD 7 min 220&254), m/z=449.0 [M+H]⁺.

2.14 Synthesis of 4-(4-(3-amino-5-chloropyridin-2-yl)-3-(4-chlorophenyl)piperazin-1-yl)-4-oxobutanoic acid (Compound 10)

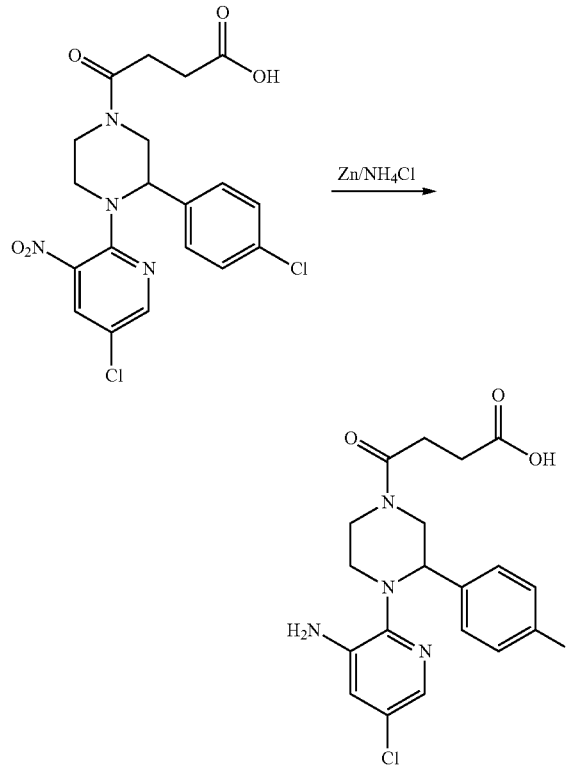

Compound 10 was prepared according to the general procedure C. Yield: 5.34% (96.98% purity). $^1$H NMR (400 MHz, CDCl$_3$) 7.57-7.54 (m, 1H), 7.25-7.12 (m, 4H), 6.87 (s, 1H), 4.77-4.60 (m, 1H), 4.56-4.43 (m, 1H), 4.01-3.86 (m, 1H), 3.53-3.28 (m, 1H), 3.30-3.14 (m, 2H), 3.09-2.98 (m, 1H), 2.80-2.72 (m, 4H) LC-MS: $t_R$=3.095 min (10-80AB_7min_220&254), m/z=423.0 [M+H]$^+$.

2.15 Synthesis of 2-(4-(3-amino-5-chloropyridin-2-yl)-3-(4-chlorophenyl)piperazine-1-carboxamido)acetic acid (Compound 11)

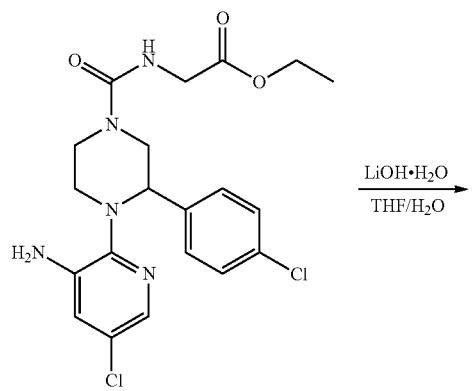

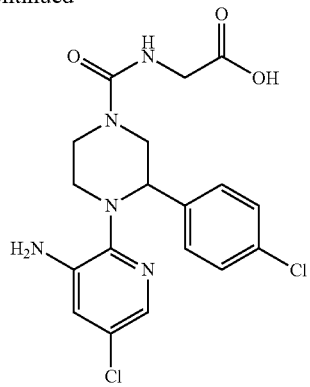

Compound 11 was prepared according to the general procedure A. Yield: 37.37% (92.25% purity). $^1$H NMR (400 MHz, CDCl$_3$) 7.47 (s, 1H), 7.21-7.02 (m, 4H), 6.84 (s, 1H), 5.96 (br s, 1H), 5.02 (br s, 2H), 4.44 (d, J=9.2 Hz, 1H), 4.08-3.72 (m, 4H), 3.23-2.57 (m, 4H) LC-MS: $t_R$=1.968 min (10-80NEU_7min_220&254), m/z=424.1 [M+H]$^+$.

2.16 Synthesis of 1-(4-(3-amino-5-chloropyridin-2-yl)-3-(4-chlorophenyl)piperazin-1-yl)-2-(piperazin-1-yl)ethanone (Compound 12)

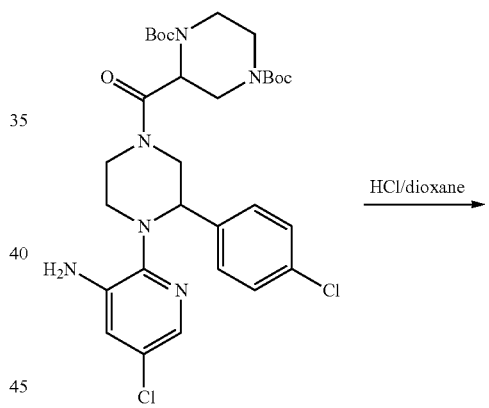

Compound 12 was prepared according to the general procedure B. Yield: 44.06% (88.02% purity). $^1$H NMR (400 MHz, DMSO-d$_6$) 10.00 (s, 1H), 9.48 (s, 1H), 7.45-7.40 (m, 1H), 7.36-7.31 (m, 2H), 7.29-7.24 (m, 2H), 6.94-6.93 (m, 1H), 5.23-4.90 (m, 2H), 4.67-4.51 (m, 1H), 4.46-4.19 (m, 3H), 3.34-3.10 (m, 6H), 2.99 (s, 1H), 2.76-2.65 (m, 1H) LC-MS: $t_R$=3.288 min (10-80CD_7min_220&254), m/z=435.1 [M+H]$^+$.

2.17 Synthesis of 1-(4-(3-amino-5-chloropyridin-2-yl)-3-(4-chlorophenyl)piperazin-1-yl)-2-(piperazin-1-yl)ethanone (Compound 13)

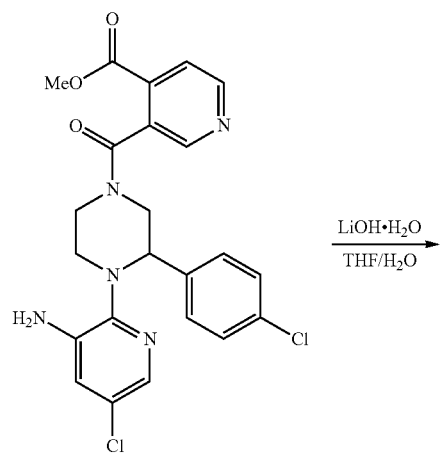

Compound 13 was prepared according to the general procedure A. Yield: 64.36% (100% purity). $^1$H NMR (400 MHz, CDCl$_3$) 8.82-8.80 (m, 1H), 8.68 (s, 1H), 7.99-7.87 (m, 1H), 7.57-7.54 (m, 1H), 7.29 (s, 1H), 7.19-7.17 (m, 1H), 7.09 (s, 2H), 6.91 (s, 1H), 5.03-4.79 (m, 1H), 4.78-4.51 (m, 1H), 3.80-3.53 (m, 2H), 3.37-3.34 (m, 1H), 3.28-3.25 (m, 2H), 3.13-2.92 (m, 2H) LC-MS: $t_R$=2.978 min (10-80AB_7min_220&254), m/z=471.9 [M+H]$^+$.

2.18 Synthesis of 3-(4-(3-amino-5-chloropyridin-2-yl)-5-(4-chlorophenyl)-2-isobutylpiperazin-1-yl)-3-oxopropanoic acid (Compound 14)

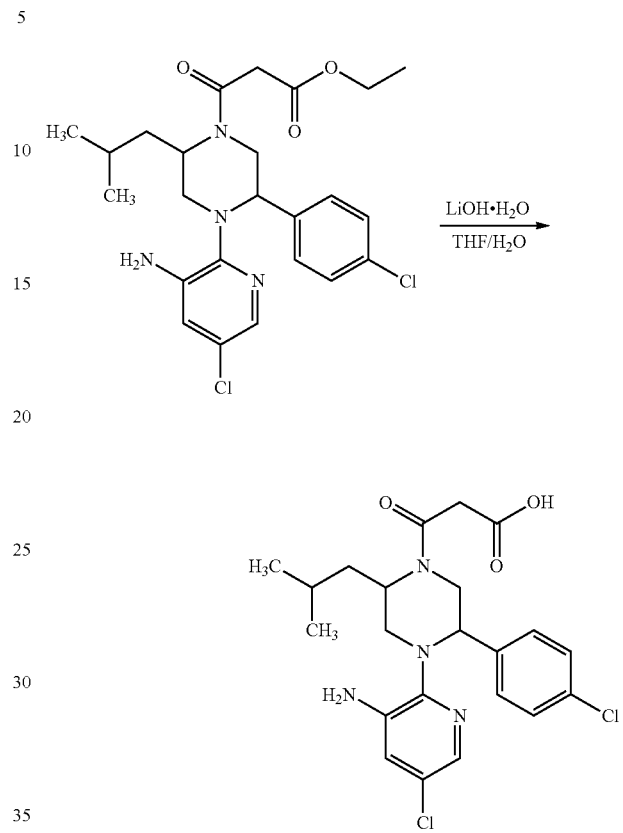

Compound 14 was prepared according to the general procedure A. Yield: 36.65% (95.19% purity). $^1$H NMR (400 MHz, CDCl$_3$) 7.62-7.52 (m, 1H), 7.26-7.16 (m, 4H), 6.95-6.88 (m, 1H), 4.98-4.47 (m, 2H), 4.02-3.32 (m, 4H), 3.19-3.05 (m, 1H), 3.03-2.89 (m, 1H), 2.18-1.97 (m, 1H), 1.84-1.50 (m, 2H), 1.10-0.99 (m, 6H); LC-MS: $t_R$=3.846 min (10-80AB_7min_220&254), m/z=465.0 [M+H]$^+$.

2.19 Synthesis of 3-((cis)-3,4-bis(4-chlorophenyl)-5-methylpiperazin-1-yl)-3-oxopropanoic acid (Compound 15)

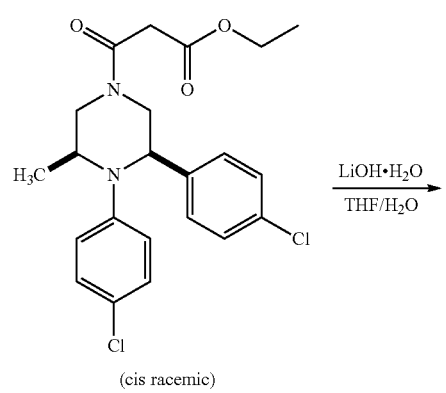

(cis racemic)

-continued

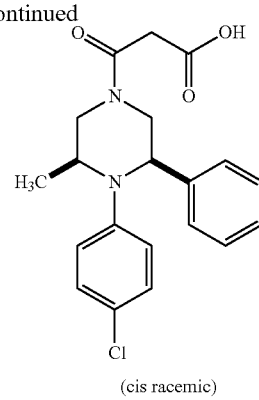

(cis racemic)

Compound 15 was prepared according to the general procedure A. Yield: 49.49% (95.459% purity). $^1$H NMR (400 MHz, CDCl$_3$) 7.24-6.81 (m, 8H), 4.79-4.57 (m, 2H), 4.38-4.04 (m, 1H), 3.95-3.66 (m, 1H), 3.61-2.68 (m, 4H), 1.13-0.92 (m, 3H) LC-MS: $t_R$=3.888 min (10-80AB_7min_220&254), m/z=406.9 [M+H]$^+$.

2.20 Synthesis of 3-((cis)-3,4-bis(4-chlorophenyl)-5-ethylpiperazin-1-yl)-3-oxopropanoic acid (Compound 16)

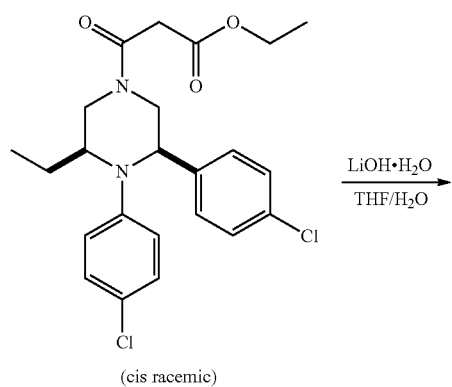

(cis racemic)

Compound 16 was prepared according to the general procedure A. Yield: 88.88% (100% purity). $^1$H NMR (400 MHz, CDCl$_3$) 7.22-7.07 (m, 6H), 6.95-6.86 (m, 2H), 4.71-4.51 (m, 1H), 4.11-4.01 (m, 1H), 3.91-3.69 (m, 1H), 3.56-3.29 (m, 3H), 3.11-2.86 (m, 2H), 1.44-1.26 (m, 2H), 0.87 (t, J=7.6 Hz, 3H) LC-MS: $t_R$=4.147 min (10-80AB_7min_220&254), m/z=421.0 [M+H]$^+$.

2.21 5-(4-(3-amino-5-chloropyridin-2-yl)-3-(4-chlorophenyl)piperazin-1-yl)-5-oxopentanoic acid (Compound 17)

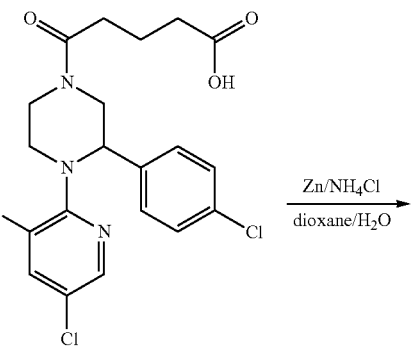

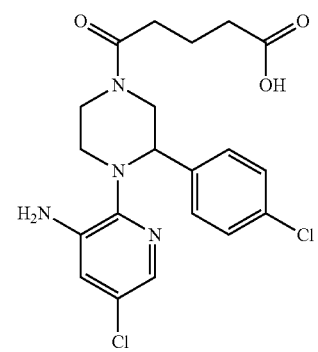

Compound 17 was prepared according to the general procedure C. Yield: 17.31% (95.55% purity). $^1$H NMR (400 MHz, CDCl$_3$) 7.57-7.54 (m, 1H), 7.23-7.13 (m, 4H), 6.88-6.87 (m, 1H), 4.75-4.62 (m, 1H), 4.52-4.43 (m, 1H), 3.98-3.88 (m, 1H), 3.53-3.44 (m, 1H), 3.25-3.17 (m, 2H), 3.02-2.97 (m, 1H), 2.86-2.80 (m, 1H), 2.76-2.60 (m, 1H), 2.57-2.40 (m, 4H), 2.07-1.97 (m, 2H) LC-MS: $t_R$=3.020 min (10-80AB_7min_220&254), m/z=436.8 [M+H]$^+$.

2.22 Synthesis of 5-(4-(3-amino-5-chloropyridin-2-yl)-3-(4-chlorophenyl)piperazin-1-yl)-5-oxopentanoic acid (Compound 18)

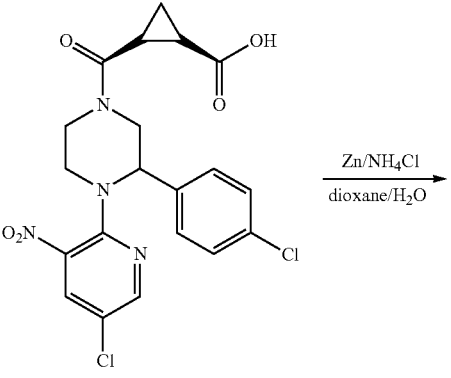

-continued

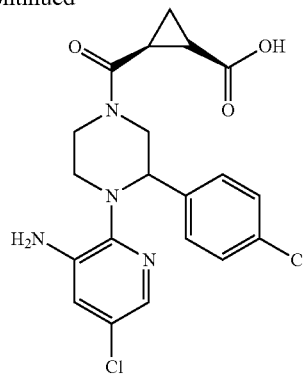

Compound 18 was prepared according to the general procedure C. Yield: 25.35% (100% purity). $^1$H NMR (400 MHz, CDCl$_3$) 7.59-7.50 (m, 1H), 7.30 (s, 1H), 7.24-7.12 (m, 3H), 7.01-6.85 (m, 1H), 4.82-4.39 (m, 3H), 4.31-3.54 (m, 2H), 2.96-2.70 (m, 2H), 2.27-2.07 (m, 2H), 1.84 (s, 1H), 1.55-1.30 (m, 1H) LC-MS: $t_R$=2.953, 3.034 min (10-80AB_7min_220&254), m/z=435.0 [M+H]$^+$.

2.23 Synthesis of 2-(4-(3-amino-5-chloropyridin-2-yl)-3-(4-chlorophenyl)piperazine-1carbonyl)cyclobutanecarboxylic acid (Compound 19)

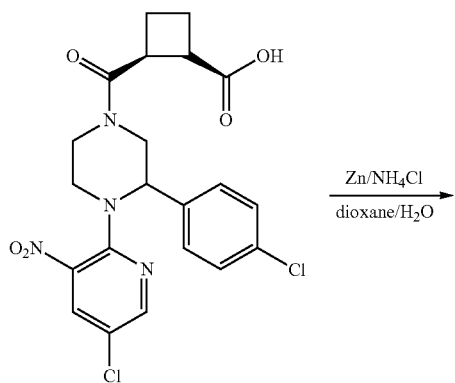

Compound 19 was prepared according to the general procedure C. Yield: 2.63% (98.68% purity). $^1$H NMR (400 MHz, CDCl$_3$) 7.59-7.50 (m, 1H), 7.30 (s, 1H), 7.24-7.12 (m, 3H), 7.01-6.85 (m, 1H), 4.82-4.39 (m, 3H), 4.31-3.54 (m, 2H), 2.96-2.70 (m, 2H), 2.27-2.07 (m, 2H), 1.84 (s, 1H), 1.55-1.30 (m, 1H) LC-MS: $t_R$=2.953, 3.034 min (10-80AB_7min_220&254), m/z=435.0 [M+H]$^+$.

2.24 Synthesis of 3-((cis)-3,4-bis(4-chlorophenyl)-5-cyclopropylpiperazin-1-yl)-3-oxopropanoic acid (Compound 20)

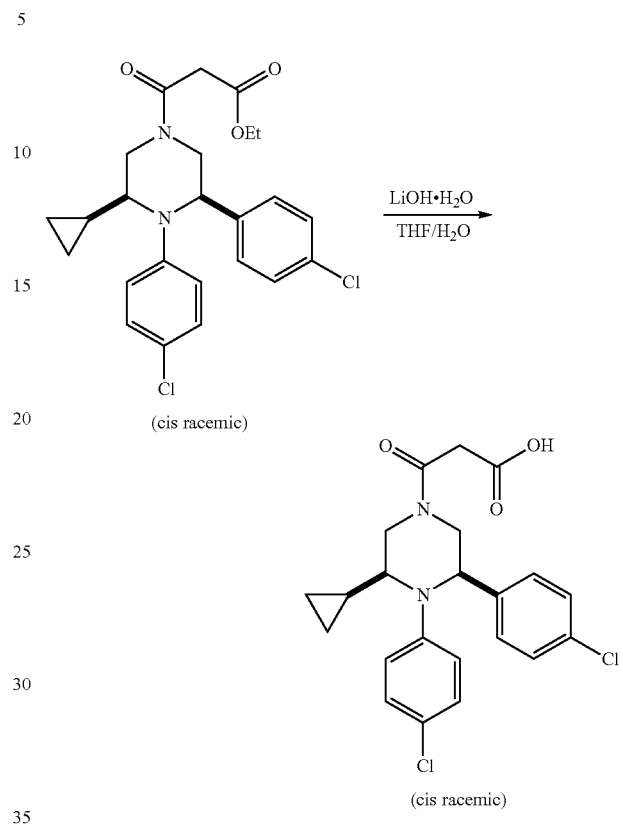

Compound 20 was prepared according to the general procedure A. Yield: 55.37% (100% purity). $^1$H NMR (400 MHz, CDCl$_3$) 7.23-7.10 (m, 6H), 7.02-6.93 (m, 2H), 4.80-4.52 (m, 1H), 4.10-4.02 (m, 1H), 3.97-3.70 (m, 1H), 3.53-3.30 (m, 3H), 3.07-2.81 (m, 1H), 2.07-1.93 (m, 1H), 0.72-0.61 (m, 1H), 0.53-0.37 (m, 1H), 0.17-0.07 (m, 2H), -0.52-0.69 (m, 1H) LC-MS: $t_R$=4.157 min (10-80AB_7min_220&254), m/z=433.0 [M+H]$^+$.

2.25 Synthesis of 3-((cis)-3,4-bis(4-chlorophenyl)-5-isobutylpiperazin-1-yl)-3-oxopropanoic acid (Compound 21)

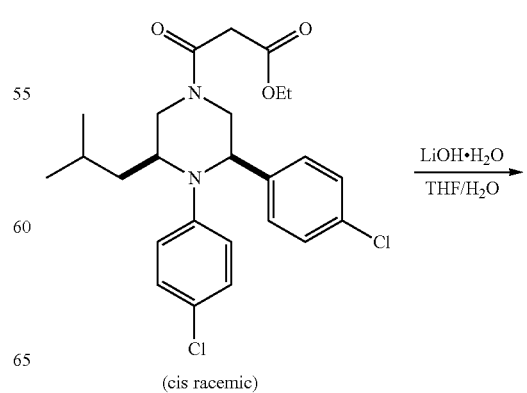

-continued

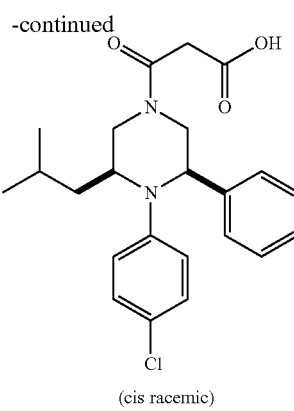

(cis racemic)

Compound 21 was prepared according to the general procedure A. Yield: 97.74%; (100% purity). $^1$H NMR (400 MHz, CDCl$_3$) 7.21-7.07 (m, 6H), 6.95-6.89 (m 2H), 4.80-4.49 (m, 1H), 4.17-4.01 (m, 1H), 3.94-3.69 (m, 1H), 3.52-3.32 (m, 2H), 3.28-2.72 (m, 3H), 1.60-1.46 (m, 1H), 1.25-1.00 (m, 2H), 0.87-0.81 (m, 3H), 0.79-0.73 (m, 3H) LC-MS: t$_R$=4.545 min (10-80AB_7min_220&254), m/z=449.1 [M+H]$^+$.

2.26 Synthesis of 3-(4-(3-amino-5-chloropyridin-2-yl)-3-(4-chlorophenyl)piperazin-1-yl)-N-methyl-3-oxopropanamide (Compound 22)

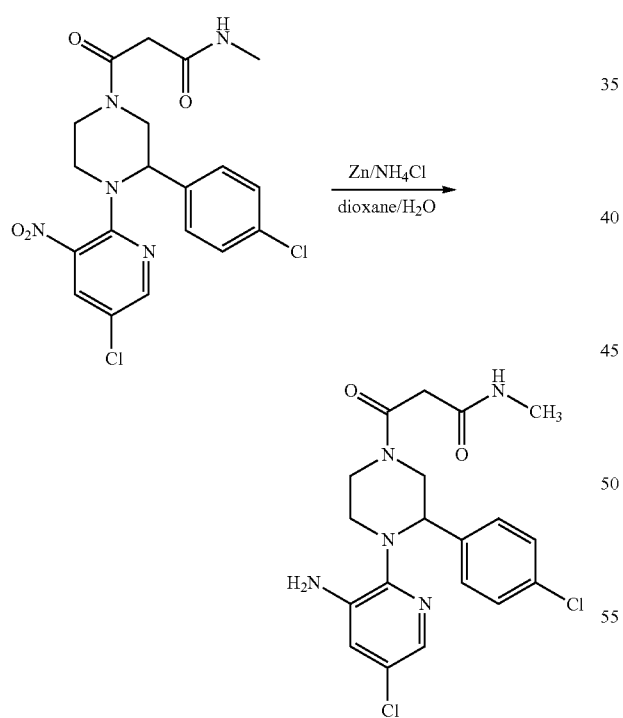

Compound 22 was prepared according to the general procedure C. Yield: 7.16% (98.357% purity). $^1$H NMR (400 MHz, CDCl$_3$) 7.59 (d, J=3.6 Hz, 1H), 7.30 (s, 2H), 7.22-7.17 (m, 2H), 6.91 (s, 1H), 4.79-4.54 (m, 2H), 4.18-4.00 (m, 1H), 3.73 (s, 1H), 3.48-3.19 (m, 4H), 3.17-2.94 (m, 2H), 2.87-2.85 (m, 3H) LC-MS: t$_R$=3.387 min (10-80CD_7min_220&254), m/z=422.0 [M+H]$^+$.

2.27 Synthesis of 2-(4-(3-amino-5-chloropyridin-2-yl)-3-(4-chlorophenyl)piperazin-1-yl)-N-methylacetamide (Compound 23)

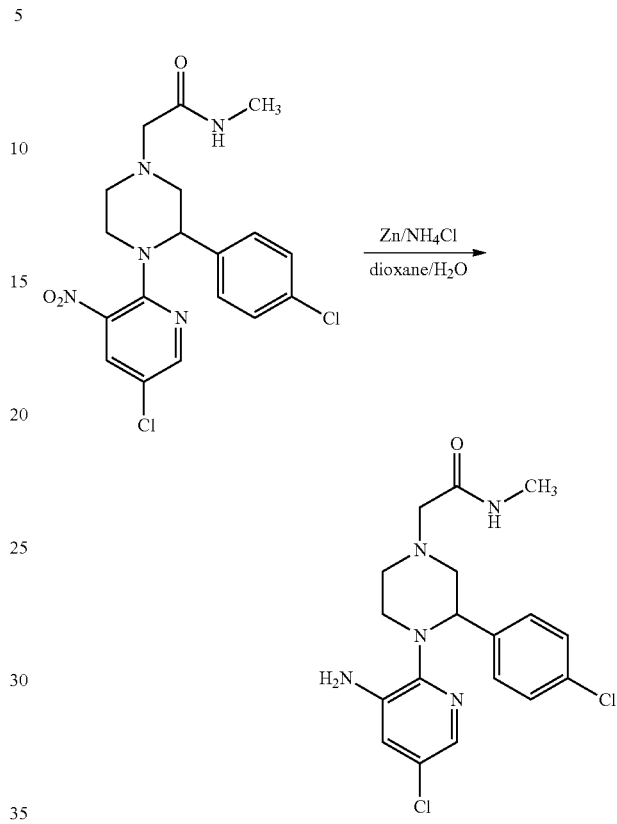

Compound 23 was prepared according to the general procedure C. Yield: 62.75% (95.25% purity). $^1$H NMR (400 MHz, CDCl$_3$) 7.57 (d, J=2.0 Hz, 1H), 7.21-7.16 (m, 2H), 7.15-7.11 (m, 2H), 6.85 (d, J=2.0 Hz, 1H), 4.64-4.60 (m, 1H), 4.14 (s, 2H), 3.22-3.14 (m, 1H), 3.11 (s, 2H), 2.98-2.84 (m, 6H), 2.71-2.59 (m, 1H), 2.49-2.43 (m, 1H) LC-MS: t$_R$=3.852 min (10-80CD_7min_220&254), m/z=394.1 [M+H]$^+$.

2.28 Synthesis of (1S,2S)-2-(4-(3-amino-5-chloropyridin-2-yl)-3-(4-chlorophenyl)piperazine-1-carbonyl)cyclopropanecarboxylic acid (Compound 24)

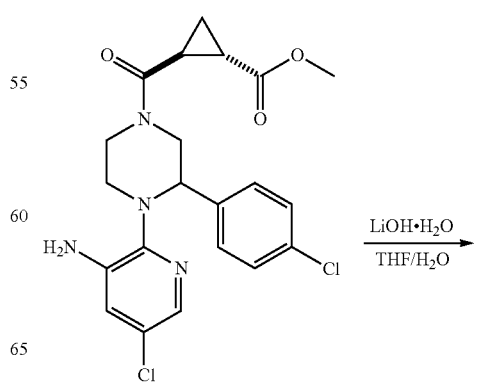

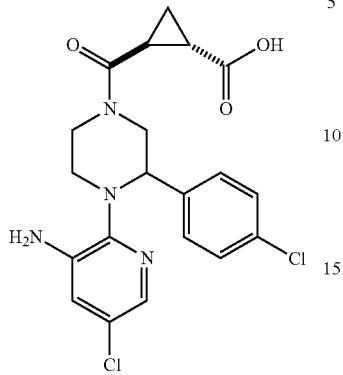

Compound 24 was prepared according to the general procedure A. Yield: 46.31% (98.49% purity). $^1$H NMR (400 MHz, CDCl$_3$) 7.65-7.50 (m, 1H), 7.26-7.06 (m, 4H), 6.95-6.80 (m, 1H), 4.74-4.38 (m, 2H), 4.30-4.06 (m, 1H), 3.77-3.74 (m, 1H), 3.62-3.26 (m, 1H), 3.23-3.14 (m, 1H), 3.08-2.67 (m, 2H), 2.45-2.34 (m, 1H), 2.33-2.20 (m, 1H), 1.89-1.81 (m, 1H), 1.61-1.52 (m, 1H), 1.50-1.37 (m, 1H) LC-MS: $t_R$=3.201 min (10-80AB_7min_220&254), m/z=434.8 [M+H]$^+$.

2.29 Synthesis of (1S,2S)-2-(4-(3-amino-5-chloropyridin-2-yl)-3-(4-chlorophenyl)piperazine-1-carbonyl)cyclobutanecarboxylic acid (Compound 25)

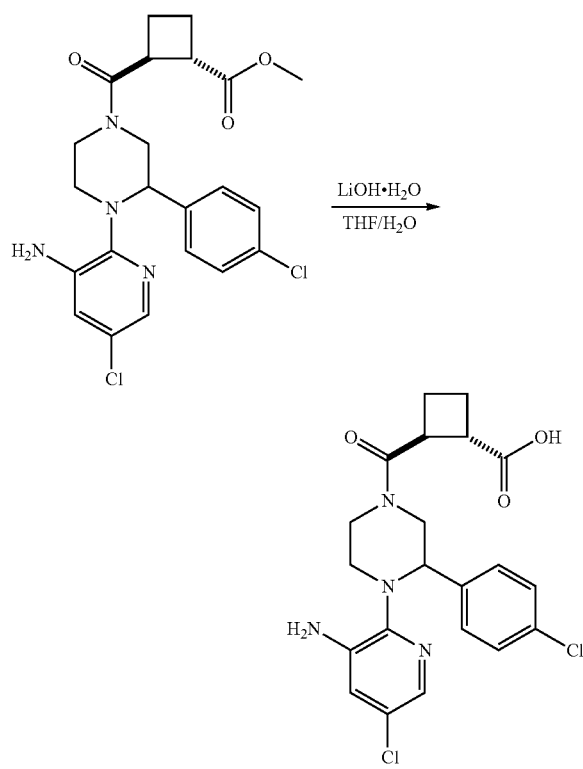

Compound 25 was prepared according to the general procedure A. Yield: 51.43% (99.742% purity). $^1$H NMR (400 MHz, CDCl$_3$) 7.60-7.51 (m, 1H), 7.23-7.07 (m, 4H), 6.90-6.84 (m, 1H), 4.77-4.53 (m, 1H), 4.48-4.39 (m, 1H), 4.29 (br s, 2H), 3.97-3.78 (m, 1H), 3.77-3.37 (m, 3H), 3.26-2.96 (m, 2H), 2.79-2.67 (m, 1H), 2.38-1.99 (m, 4H); LC-MS: $t_R$=3.426 min (10-80AB_7min_220&254), m/z=448.8 [M+H]$^+$.

2.30 Synthesis of 3-(4-(3-amino-5-chloropyridin-2-yl)-3-(4-chlorophenyl)piperazine-1-carbonyl)cyclobutanecarboxylic acid (Compound 26)

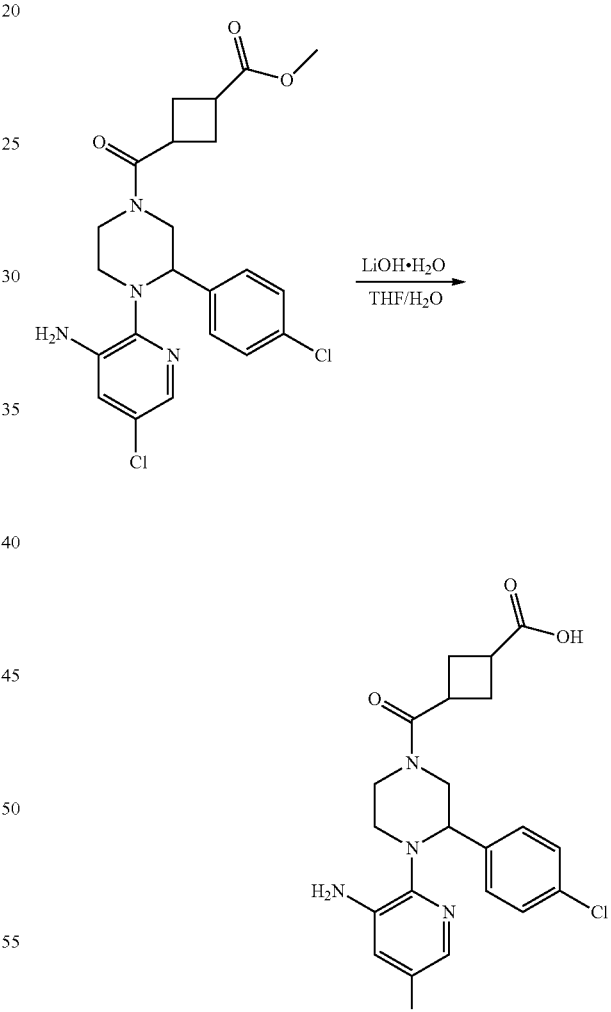

Compound 26 was prepared according to the general procedure A. Yield: 22.17%. $^1$H NMR (400 MHz, CDCl$_3$) 7.59-7.51 (m, 1H), 7.25-7.12 (m, 4H), 6.87 (d, J=1.8 Hz, 1H), 4.75-4.58 (m, 1H), 4.49-4.42 (m, 1H), 3.84-3.66 (m, 1H), 3.32-3.07 (m, 4H), 2.89-2.65 (m, 4H), 2.61-2.36 (m, 2H); LC-MS: $t_R$=3.360 min (10-80AB_7min_220&254), m/z=448.8 [M+H]$^+$.

2.31 Synthesis of 3-(4-(3-amino-5-chloropyridin-2-yl)-3-(4-chlorophenyl)piperazine-1-carbonyl)benzoic acid (Compound 27)

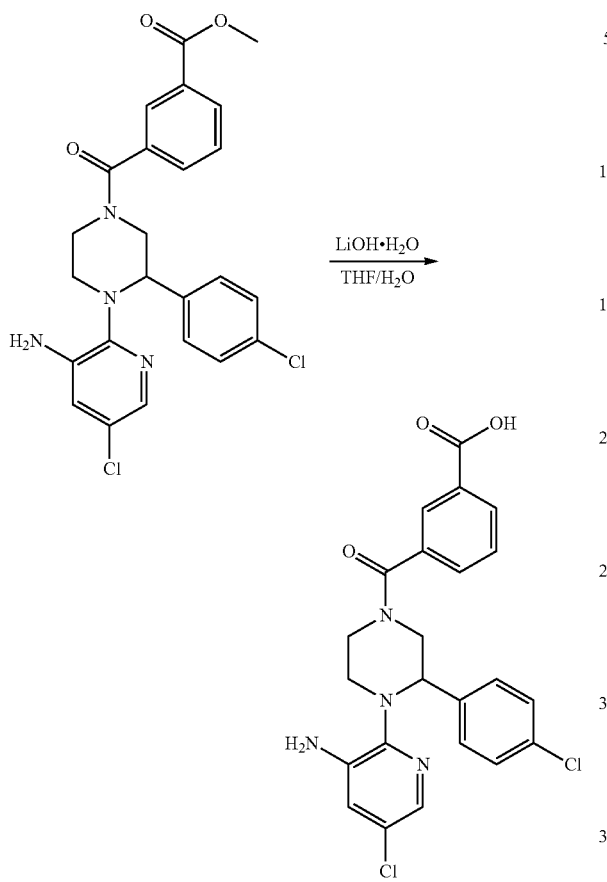

Compound 27 was prepared according to the general procedure A. Yield: 71.26% (99.29% purity). $^1$H NMR (400 MHz, DMSO-$d_6$) 8.07-7.92 (m, 2H), 7.71 (s, 1H), 7.64-7.53 (m, 1H), 7.43-7.13 (m, 5H), 6.91 (s, 1H), 5.63 (s, 2H), 4.55-4.40 (m, 2H), 3.15-2.93 (m, 3H); LC-MS: $t_R$=3.754 min (10-80AB_7min_220&254), m/z=470.7 [M+H]$^+$.

2.32 Synthesis of 4-(4-(3-amino-5-chloropyridin-2-yl)-3-(4-chlorophenyl)piperazine-1-carbonyl)benzoic (Compound 28)

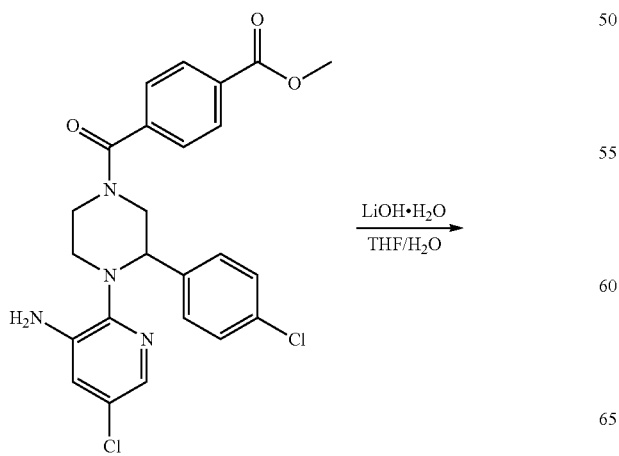

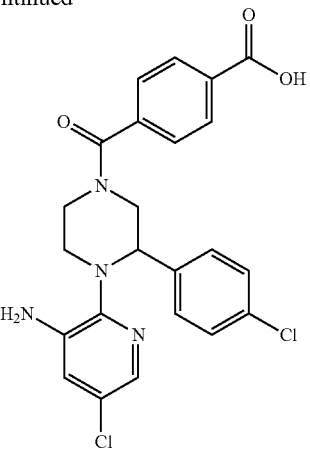

Compound 28 was prepared according to the general procedure A. Yield: 63.07% (97.44% purity). $^1$H NMR (400 MHz, DMSO-$d_6$) 8.04-7.97 (m, 2H), 7.58 (s, 2H), 7.43-7.13 (m, 5H), 6.90 (s, 1H), 5.64 (d, J=17.2 Hz, 2H), 4.57-4.41 (m, 2H), 3.23-3.03 (m, 3H); LC-MS: $t_R$=3.737 min (10-80AB_7min_220&254), m/z=470.8 [M+H]$^+$.

2.33 Synthesis of rel-3[(3R,5S)-4-(3-amino-5-chloropyridin-2-yl)-3-(4-chlorophenyl)-5-(2-methylpropyl)piperazin-1-yl]-3-oxopropanoic acid (Compound 29)

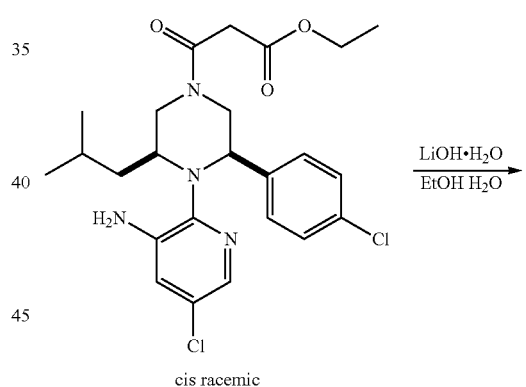

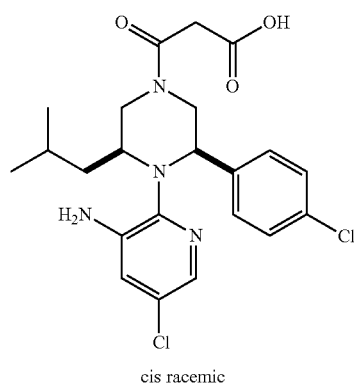

Compound 29 was prepared according to the general procedure A. Yield: 48.8% (99.54% purity). $^1$H NMR (400 MHz, CDCl$_3$) δ (ppm): 7.75-7.68 (m, 1H), 7.17-7.05 (m, 4H), 6.74-6.67 (m, 1H), 4.85 and 4.63 (d, J=13.0 Hz, 1H, rotamer), 4.33-4.18 (m, 1H), 4.17-3.98 (m, 2H), 3.98-3.86 (m, 0.5H), 3.81-3.70 (m, 0.5H), 3.54-3.09 (m, 4H), 3.05-2.94 (m, 0.5H), 2.77-2.66 (m, 0.5H), 1.55-1.16 (m, 2H, overlapped with water peak), 1.01-0.89 (m, 1H), 0.85-0.76 (m, 3H), 0.74-0.64 (m, 3H). MS: m/z 466.1 [M+1]$^+$.

2.34 Synthesis of rel-3-((3R,5S)-4-(3-amino-5-chloropyridin-2-yl)-3-(4-chlorophenyl)-5-neopentylpiperazin-1-yl)-3-oxopropanoic acid (30)

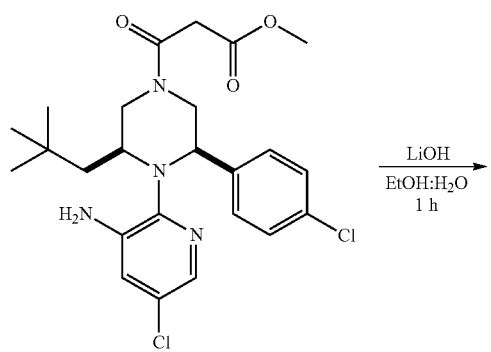

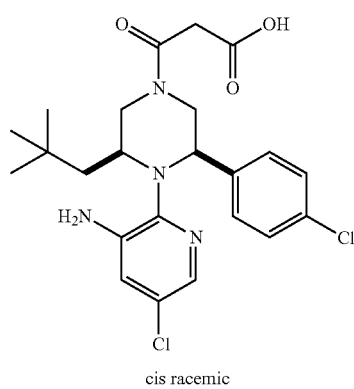

cis racemic

Compound 30 was prepared according to the general procedure A. Yield: 58%. $^1$H NMR (400 MHz, DMSO-d$_6$) δ (ppm): 7.54-7.48 (m, 1H), 7.39-7.28 (m, 2H), 7.23-7.15 (m, 2H), 6.79-6.72 (m, 1H), 5.51 (s, 2H), 4.60 (d, J=12.4 Hz, 0.5H), 4.34-4.22 (m, 1H), 4.08 (dd, J=11.3, 3.0 Hz, 0.5H), 3.88 (d, J=13.2 Hz, 0.5H), 3.70 (d, J=12.9 Hz, 0.5H), 3.53-3.42 (m, 2H, overlapped with solvent peak), 3.20-2.97 (m, 1H), 2.89-2.65 (m, 2H), 1.19-1.03 (m, 2H), 0.61 and 0.60 (s, 9H, rotamer). MS: m/z 480.9 [M+1]$^+$.

2.35 Synthesis of rel-3-((3R,5S)-4-(3-amino-5-chloropyridin-2-yl)-3-(4-chlorophenyl)-5-(cyclopentylmethyl)piperazin-1-yl)-3-oxopropanoic acid (31)

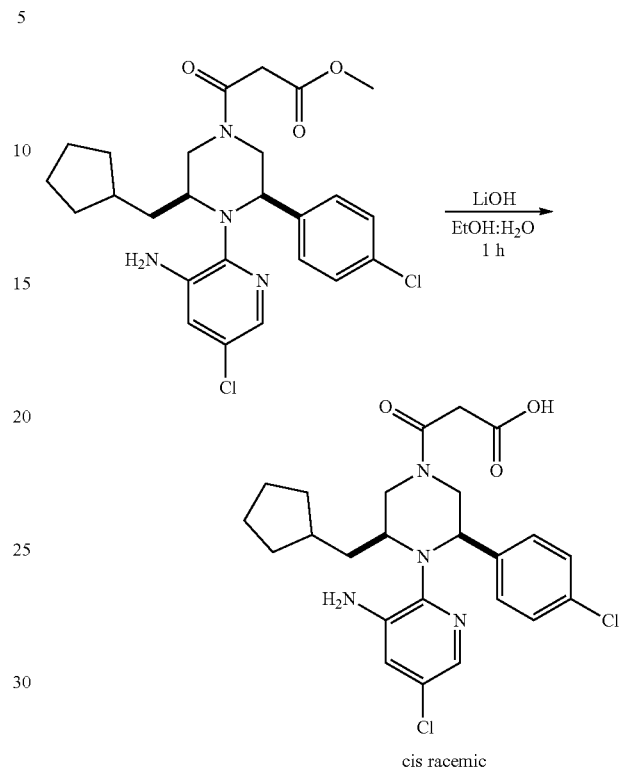

cis racemic

Compound 31 was prepared according to the general procedure A. Yield: 26%. $^1$H NMR (400 MHz, DMSO-d$_6$) δ (ppm): 7.50 (d, J=2.4 Hz, 1H), 7.37-7.28 (m, 2H), 7.22-7.15 (m, 2H), 6.76-6.70 (m, 1H), 5.51 and 5.50 (s, 2H, rotamer), 4.62 (d, J=12.4 Hz, 0.5H), 4.33-4.19 (m, 1H), 4.07-3.96 (m, 1H), 3.73 (d, J=12.9 Hz, 0.5H), 3.43-3.39 (m, 1H, overlapped with solvent), 3.20-2.93 (m, 2H), 2.90-2.64 (m, 2H), 1.73-1.54 (m, 3H), 1.52-1.34 (m, 5H), 0.99-0.77 (m, 2H), 0.74-0.51 (m, 1H). MS: m/z 492.9 [M+1]$^+$.

Example 3

Fluorescence Polarization (FP) Experiment Procedure

The compounds binding to MDM2 were determined by a quantitative fluorescence polarization binding assay using a recombinant MDM2 protein and fluorescently labeled peptide probes using a BioTek Cytation 5 machine. Compounds were tested in 10% DMSO, 100 mM potassium phosohate pH 7.2, 100 ug/ml bovine γ-globulin, 0.02% (w/v) sodium azideand 0.01% (v/v) triton X-100. KI values of tested compounds were determined in a dose-dependent competitive binding experiment by fitting the sigmoidal dose-dependent FP increases as a function of protein concentrations using Graphpad Prism software.

Isothermal Titration Calorimetry (ITC) Experimental Procedure

ITC experiments were run on a Malvern MicroCal Auto-ITC200 or ITC200 machine. Titration experiments were run in 20 mM Phosphate, 150 mM NaCl and 1 mM DTT at pH 7.3. Compounds were loaded in the syringe and tested at mM concentrations with DMSO up to 6.5%. MDM2 protein concentrations in the cell ranged from 20-100 μM.

TABLE 2

Biophysical data for the MDM2 binders. Selected compounds were also tested using Isothermal Titration Calorimetry.

| Compound No. | Fluorescence Polarization Assay KI (µM) | Isothermal Titration Calorimetry KD (µM) |
| --- | --- | --- |
| 1 | 92 | 95 |
| 2 | 118 | ND |
| 3 | 29 | 22 |
| 4 | 107 | ND |
| 5 | 28 | 24 |
| 6 | 68 | 34 |
| 7 | 18 | 18 |
| 8 | 11 | ND |
| 9 | >250 | ND |
| 10 | 39 | 32 |
| 11 | 16 | 20 |
| 12 | >250 | ND |
| 13 | 13 | ND |
| 14 | 23 | ND |
| 15 | 9 | 7.5 |
| 16 | 4 | ND |
| 17 | 60 | 15 |
| 18 | 106 | 70 |
| 19 | 140 | 230 |
| 20 | 6 | ND |
| 21 | 1.5 | 0.4 |
| 22 | 61 | 76 |
| 23 | 75 | ND |
| 24 | 34 | ND |
| 25 | 61 | ND |
| 26 | 22 | ND |
| 27 | 36 | ND |
| 28 | 46 | ND |
| 29 | 0.5 | 1.0 |
| 30 | 0.8 | ND |
| 31 | 0.3 | ND |

ND = Not determined

Example 4

Thermal Shift Experimental Procedure

Qualitative evaluation of compound binding to MDM2 was determined using a fluorescence-based thermal shift assay with a Roche LC480 lightcycler. Each experiment was performed in ~30 mins with ramping up of temperature to monitor thermal denaturation of MDM2. Compounds at 0.16 mM, 0.08 mM and 0.04 mM were added to recombinant MDM2 protein and SYPRO orange dye in 5% DMSO 50 mM Bis-Tris Propane pH 8.0 and 100 mM NaCl. Positive thermal shift was indicative of compound binding to the proteins of interest.

TABLE 3

Thermal shift data for the MDM2 inhibitors.

| Compound No. | Thermal Shift 0.16 mM (° C.) | Thermal Shift 0.08 mM (° C.) | Thermal Shift 0.04 mM (° C.) |
| --- | --- | --- | --- |
| 1 | 2.0 | 1.0 | 0.6 |
| 2 | 0.6 | 0 | 0 |
| 3 | 3.0 | 2.0 | 1 |
| 4 | 1.0 | 0.5 | 0 |
| 5 | 2.0 | 1.0 | 1.0 |
| 6 | 2.0 | 1.0 | 0.3 |
| 7 | 2.0 | 1.0 | 1.0 |
| 8 | −0.4 | −0.1 | 0 |
| 9 | 0.6 | 0.2 | 0.1 |
| 10 | 2.0 | 1.0 | 1.0 |
| 11 | 2.0 | 1.0 | 1.0 |
| 12 | 1.0 | 0.4 | 0 |
| 13 | 1.0 | 1.0 | 0.4 |
| 14 | ND | ND | ND |
| 15 | 2.0 | 2.0 | 1.0 |
| 16 | 2.0 | 2.0 | 2.0 |
| 17 | ND | ND | ND |
| 18 | ND | ND | ND |
| 19 | ND | ND | ND |
| 20 | ND | ND | ND |
| 21 | −4.0 | 3.0 | 4.0 |
| 22 | ND | ND | ND |
| 23 | ND | ND | ND |
| 24 | ND | ND | ND |
| 25 | ND | ND | ND |
| 26 | ND | ND | ND |
| 27 | ND | ND | ND |
| 28 | ND | ND | ND |
| 29 | 12.0 | 9.0 | 7.0 |
| 30 | 11.0 | 9.0 | 7.0 |
| 31 | 11.0 | 10.0 | 8.0 |

ND = Not determined

Example 6

10 µM of the following compounds were tested for ability to inhibit MDM2. Hep G2 cells were treated with 10 µM of the compounds for 1 h and 2 h. Since MDM2 activity results in p53 degradation, the ability of the compounds to increase p53 protein content was used as readout for MDM2 inhibition. p53 protein levels were assayed by western blot and level of p53 protein relative to untreated control was determined by densitometry analysis. The results are displayed in Table 4.

TABLE 4

| Compound No. | Fold change of p53 levels after 1 h treatment with compound | Fold change of p53 levels after 2 h treatment with compound |
| --- | --- | --- |
| 21 | 1.14 | 1.29 |
| 29 | 1.40 | 1.34 |
| 30 | 1.37 | 1.04 |
| 31 | 1.13 | 0.98 |

What is claimed is:

1. An inhibitor of MDM2 according to Formula I:

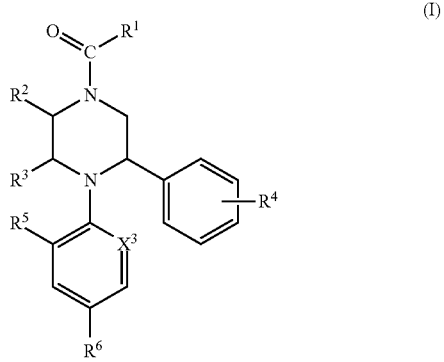

(I)

wherein

R$^1$ is C$_1$-C$_6$ substituted alkyl substituted with a member selected from C(O)R$^{11}$, (=O), and NR$^{13}$R$^{14}$, in which R$^{11}$ is selected from H, OR$^{13}$, and substituted or unsubsituted alkyl, substituted or unsubsituted heteroalkyl,
wherein
R$^{13}$ and R$^{14}$ are independently selected from H, substituted or unsubstituted alkyl and substituted or unsubstituted heteroalkyl, and R$^{13}$ and R$^{14}$, together with the nitrogen to which they are bound, are optionally joined to form a ring of 4, 5 or 6 members, which is selected from substituted or unsubstituted cycloalkyl, substituted or unsubstituted heterocycloalkyl, substituted or unsubstituted aryl and substituted or unsubstituted heteroaryl;
R$^2$, and R$^3$ are independently selected from H, and unsubstituted C$_1$-C$_8$ straight-chain, branched chain and cyclic alkyl;
R$^4$ is halo;
R$^5$ is independently selected from H, amine and substituted or unsubstituted alkylamine;
R$^6$ is selected from halo, and CF$_3$; and
X$^3$ is selected from N and CH.

2. The inhibitor of MDM2 according to claim 1, wherein R$^4$ is chloro.

3. The inhibitor of MDM2 according to claim 1, wherein one of R$^2$ and R$^3$ is selected from unsubstituted C$_1$-C$_6$ straight-chain, branched-chain, and cyclic alkyl.

4. The inhibitor of MDM2 to claim 1, wherein R$^5$ is NH$_2$.

5. The inhibitor of MDM2 according to claim 1, wherein R$^6$ is chloro.

6. The inhibitor of MDM2 of claim 1 according to the formula:

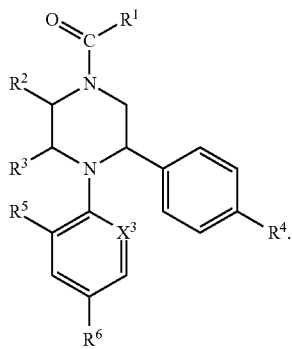

7. The inhibitor of MDM2 of claim 1 according to the formula:

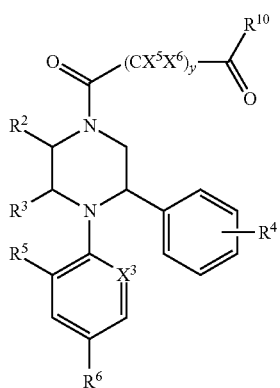

wherein,
each X$^5$ and X$^6$ is independently selected from:
(i) H, and substituted or unsubstituted alkyl; and
(ii) one or more pair of X$^5$ and X$^6$, together with the carbon to which they are each bound, are (C=O);
y is 1, 2, 3, 4, 5, or 6;
R$^{10}$ is selected from OR$^{13}$, NR$^{13}$R$^{14}$
wherein
R$^{13}$ and R$^{14}$ are independently selected from H, substituted or unsubstituted alkyl and substituted or unsubstituted heteroalkyl, and R$^{13}$ and R$^{14}$, together with the nitrogen to which they are bound, are optionally joined to form a ring of 4, 5 or 6 members, which is selected from substituted or unsubstituted cycloalkyl, substituted or unsubstituted heterocycloalkyl, substituted or unsubstituted aryl and substituted or unsubstituted heteroaryl.

8. The inhibitor of MDM2 of claim 7 according to the formula:

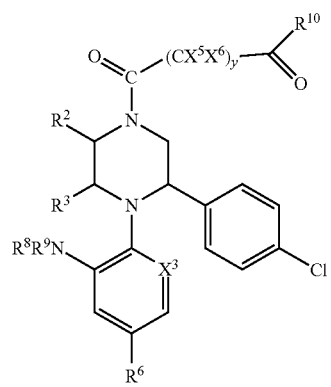

wherein R$^8$ and R$^9$ are independently selected from H, acyl, substituted or unsubstituted alkyl and substituted or unsubstituted heteroalkyl.

9. A pharmaceutical formulation comprising a compound according to claim 1, or a pharmaceutically acceptable salt thereof, and a pharmaceutically acceptable carrier, adjuvant, or vehicle.

10. A method of inhibiting MDM2 in a biological sample comprising contacting the sample with the inhibitor of MDM2 of claim 1.

11. A method of treating a MDM2-mediated disorder, disease, or condition in a patient comprising administering to said patient the pharmaceutical formulation of claim 9.

12. The method of claim 11, wherein the disorder is selected from an autoimmune disorder, an inflammatory disorder, a proliferative disorder, an endocrine disorder, a neurological disorder, or a disorder associated with transplantation.

13. The method of claim 12, wherein the proliferative disorder is a cancer.

14. The compound inhibitor of MDM2 according to claim 8, wherein R$^2$ is H; R$^3$ is unsubstituted branched-chain alkyl; and X$^3$ is N.

15. A compound according to a formula selected from:
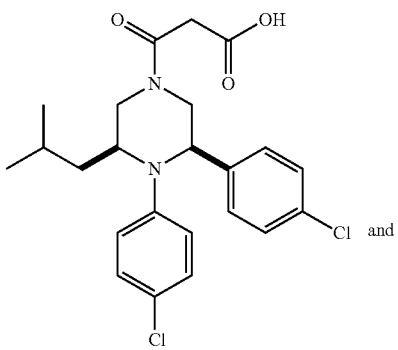
(cis racemic)
and
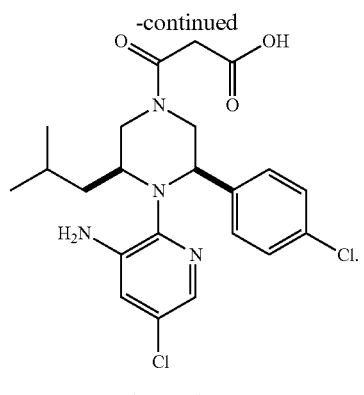
(cis racemic)
* * * * *